US009964608B2

(12) United States Patent
Diamond et al.

(10) Patent No.: US 9,964,608 B2
(45) Date of Patent: May 8, 2018

(54) METHOD AND APPARATUS FOR NONLINEAR SUSCEPTIBILITY MAGNITUDE IMAGING OF MAGNETIC NANOPARTICLES

(71) Applicant: The Trustees of Dartmouth College, Hanover, NH (US)

(72) Inventors: Solomon G. Diamond, Hanover, NH (US); Bradley W. Ficko, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days. days.

(21) Appl. No.: 15/309,201

(22) PCT Filed: May 6, 2015

(86) PCT No.: PCT/US2015/029481
§ 371 (c)(1),
(2) Date: Nov. 6, 2016

(87) PCT Pub. No.: WO2015/171773
PCT Pub. Date: Nov. 12, 2015

(65) Prior Publication Data
US 2017/0067972 A1    Mar. 9, 2017

Related U.S. Application Data

(60) Provisional application No. 61/989,986, filed on May 7, 2014.

(51) Int. Cl.
G01N 27/84 (2006.01)
G01R 33/12 (2006.01)
(Continued)

(52) U.S. Cl.
CPC ........ *G01R 33/1276* (2013.01); *A61B 5/0515* (2013.01); *A61N 1/403* (2013.01)

(58) Field of Classification Search
CPC ................ G01R 33/12; G01R 33/1276; G01R 33/0213; G01R 33/10; G01R 33/1269;
(Continued)

(56) References Cited

U.S. PATENT DOCUMENTS 5,622,169 A     4/1997  Golden
2003/0085703 A1*  5/2003  Gleich .................... A61B 5/05
                                                        324/309
(Continued)

FOREIGN PATENT DOCUMENTS

WO     2014031985 A1    2/2014

OTHER PUBLICATIONS

PCT/US2015/029481 International Search Report & Written Opinion dated Aug. 13, 2015, 8 pages.
(Continued)

*Primary Examiner* — Thang Le
(74) *Attorney, Agent, or Firm* — Lathrop Gage LLP

(57) ABSTRACT

A magnetic nanoparticle imaging system has driving coils driven at multiple frequencies, the driving coils positioned to provide magnetic fields and field gradients to an imaging zone, and a static bias field magnet positioned to provide a static magnetic field and/or field gradient to the imaging zone. Magnetic sensors are positioned to sense magnetic fields from the imaging zone, and a signal processor processes signals from the sensors to find at least signal magnitude and phase at harmonics and/or intermodulation products of the multiple frequencies. In embodiments, the signal processing apparatus also determines signal magnitudes and phase of at least second and third harmonics of the first frequency, and maps location of nanoparticles in the
(Continued)

imaging zone based upon the magnitudes of harmonics and magnitudes of the intermodulation products.

21 Claims, 15 Drawing Sheets

(51) Int. Cl.
*A61B 5/05* (2006.01)
*A61N 1/40* (2006.01)

(58) Field of Classification Search
CPC ............ G01R 33/4808; G01R 33/5601; G01N 27/72; A61B 5/05; A61B 5/0515; A61B 5/7257; A61N 1/403
USPC ........ 324/214, 201, 203, 224, 216; 600/407, 600/408, 424, 105
See application file for complete search history.

(56) References Cited

U.S. PATENT DOCUMENTS

| | | | |
|---|---|---|---|
| 2007/0020701 A1* | 1/2007 | Menon | G01N 24/08 435/7.5 |
| 2008/0218162 A1 | 9/2008 | Ruhrig | |
| 2009/0143665 A1 | 6/2009 | Seki et al. | |
| 2009/0309597 A1 | 12/2009 | Horack et al. | |
| 2010/0219825 A1 | 9/2010 | Sato et al. | |
| 2011/0089942 A1 | 4/2011 | Goodwill et al. | |
| 2011/0182821 A1 | 7/2011 | Gruell et al. | |
| 2011/0273176 A1* | 11/2011 | Weaver | A61B 5/05 324/301 |
| 2012/0119739 A1 | 5/2012 | Gleich | |
| 2012/0153949 A1 | 6/2012 | Biederer et al. | |
| 2012/0194198 A1 | 8/2012 | Moran | |
| 2015/0219732 A1* | 8/2015 | Diamond | A61B 5/04008 324/201 |
| 2015/0276902 A1* | 10/2015 | Weaver | G01R 33/4808 324/309 |
| 2016/0135710 A1* | 5/2016 | Goodwill | G01R 33/10 600/409 |

OTHER PUBLICATIONS

PCT/US2013/056436 International Search Report & Written Opinion dated Nov. 27, 2013, 12 pages.

PCT/US15/61851 International Search Report & Written Opinion dated Feb. 5, 2016, 11 pages.

Ficko, Bradley, W. et al: "Nonlinear susceptibility magnitude imaging of magnetic nanoparticles", Journal of Magnetism and Magnetic Materials, vol. 378, Mar. 1, 2015 (Mar. 1, 2015), 12 pp., XP055425580, Amsterdam, NL, ISSN: 0304-8853, DOI: 10.1016/j.jmmm.2014.11.049.

Knopp, T et al: "Model-Based Reconstruction for Magnetic Particle Imaging", IEEE Transactions on Medical Imaging, IEEE Service Center, Piscataway, NJ, US, vol. 29, No. 1, Jan. 1, 2010 (Jan. 1, 2010), 8 pp., XP011293583, ISSN: 0278-0062.

Extended European Search Report for 15789380.1 dated Nov. 24, 2017, 11 pp.

* cited by examiner

METHOD AND APPARATUS FOR NONLINEAR SUSCEPTIBILITY MAGNITUDE IMAGING OF MAGNETIC NANOPARTICLES

RELATED APPLICATIONS

This application is a 35 U.S.C. § 371 filing of International Application No. PCT/US2015/029481 filed 6 May 2015, which claims priority to U.S. provisional patent application 61/989,986 filed 7 May 2014, the contents of which are incorporated herein by reference. The present document is related to the material of PCT/US13/56436 filed 13 Aug. 2013, which claims priority to U.S. Provisional Patent Application 61/693,044 filed 24 Aug. 2012. The contents of these applications are incorporated herein by reference.

GOVERNMENT INTEREST

The work described herein has been made with government support through grant number 1R21EB016241-01A1 from the National Institute of Biomedical Imaging and Bioengineering, a part of the National Institutes of Health. The work has also been made with government support through grant number 5-R24-HD065703 from the National Center for Medical Rehabilitation Research, a part of the National Institutes of Health. The work has also been supported by grant number U54-CA 151662 from the National Cancer Institute, a part of the National Institutes of Health. The government has certain rights in the invention.

FIELD

The present document relates to the field of magnetic nanoparticle imaging. In particular, the document describes methods and apparatus adapted to localizing concentrations of nanoparticles, such as may be useful in medical imaging and similar applications.

BACKGROUND

The use of magnetic nanoparticles (mNPs) in medicine is an active area of research with several promising therapies and imaging modalities currently under study. One of the most promising uses of mNPs in medicine is as an imaging contrast agent.

SUMMARY

A magnetic nanoparticle or magnetic particle imaging system has driving coils driven at multiple frequencies, the driving coils positioned to provide magnetic fields and field gradients to an imaging zone, and a static bias field magnet positioned to provide a static magnetic field and/or field gradient to the imaging zone. Magnetic sensors are positioned to sense magnetic fields from the imaging zone, and a signal processor processes signals from the sensors to find at least signal magnitude and phase at harmonics and/or intermodulation products of the multiple frequencies. In embodiments, the signal processing apparatus also determines signal magnitudes and phase of at least second and third harmonics of the first frequency, and maps location of nanoparticles in the imaging zone based upon the magnitudes of harmonics and/or magnitudes of the intermodulation products.

A magnetic nanoparticle imaging system has driving coil(s) coupled to AC driving circuits operable at a first frequency and arranged to provide magnetic fields and field gradients to an imaging zone. Magnetic sensor(s) are positioned to sense magnetic fields from the imaging zone; and a signal processor measures at least magnitude and phase at harmonic(s) of the driving coil.

In another embodiment, a magnetic nanoparticle imaging system has a first driving coil coupled to a first AC driving circuit operable at a first frequency, and a second driving coil coupled to a second AC driving circuit operable at a second frequency, the first and second frequencies being different, the first and second driving coils being positioned to provide magnetic fields and field gradients to an imaging zone. The system also has at least one magnetic sensor positioned to sense magnetic fields from the imaging zone; and signal processing apparatus for determining at least magnitude and phase at intermodulation products of the first and second frequency in signals from the sensor.

In alternative embodiments, driving coils are provided at two or more frequencies, and the signal processing apparatus determines voxel locations of magnetic nanoparticle concentrations based upon harmonics of the driving frequencies as well as upon intermodulation products.

In another embodiment, a method of imaging magnetic nanoparticles in an imaging zone includes applying an AC driving magnetic field to the imaging zone at a first and a second frequency; applying a DC magnetic field gradient to the imaging zone, the DC magnetic field inadequate to saturate magnetic nanoparticles anywhere in the imaging zone. measuring magnetic fields from the imaging zone to provide data with at least two sensors; analyzing the data for phase, harmonics and intermodulation products of the first and second frequencies; and generating a map of locations and concentrations of the magnetic nanoparticles based upon the harmonics and intermodulation products of the first and second frequencies.

In another embodiment, a magnetic particle imaging system adapted for imaging nanoparticles of average diameter between 5 and 250 nanometers, or for imaging microparticles of average size between 250 and 2500 nanometers, including: at least a first and a second driving coil, the first driving coil coupled to a first AC driving circuit operable at a first frequency, the second driving coil coupled to a second AC driving circuit operable at the first frequency, the driving coils configured to provide magnetic fields and field gradients to an imaging zone; at least one magnetic sensor positioned to sense magnetic fields from the imaging zone; and signal processing apparatus for determining at least magnitude and phase of at least one harmonic frequency of the driving coil; and wherein the signal processing apparatus is further configured to map the location of magnetic nanoparticles in the imaging zone based upon at least the magnitudes and phases of the at least one harmonic of the first frequency. In this system, the first and second AC driving circuits are adapted to provide a first and a second predetermined phase shift between drive to the first driving coil at the first frequency and drive to the second driving coil at the first frequency, the first and second predetermined phase shifts being unequal.

In another embodiment, a magnetic particle imaging system adapted for imaging nanoparticles of average diameter between 5 and 250 nanometers, or for imaging microparticles of average size between 250 and 2500 nanometers, including: at least a first driving coil, the first driving coil coupled to a first AC driving circuit operable at a first frequency and configured to provide magnetic fields and field gradients to an imaging zone; at least one magnetic sensor positioned to sense magnetic fields from the imaging zone; and signal processing apparatus for determining at least magnitude and phase of at least a first harmonic frequencies of the driving coil; and wherein the signal processing apparatus is further configured to map the location of nanoparticles in the imaging zone based upon at least the magnitudes and phases of the harmonics of the first frequency, wherein the magnetic fields within the imaging zone are insufficiently strong to maintain the magnetic particles in magnetic saturation for a period in excess of a cycle of the first AC driving circuit anywhere in the imaging zone.

DETAILED DESCRIPTION OF THE EMBODIMENTS

Figure 1:
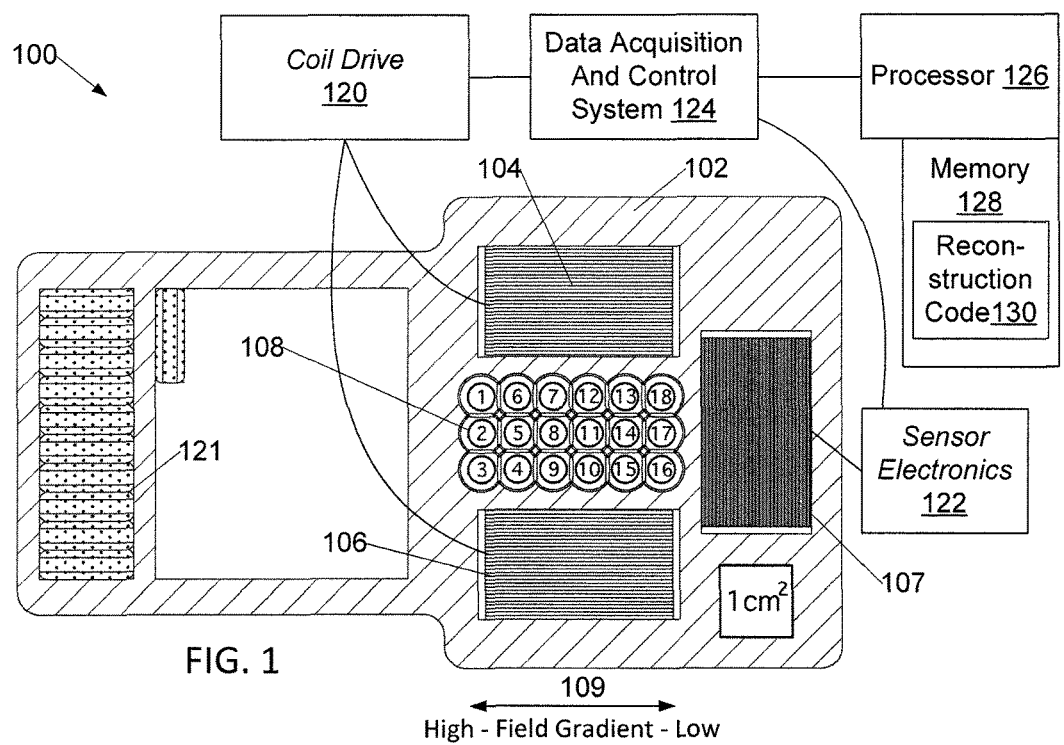
FIG. 1 is a block schematic illustration of an experimental apparatus used to demonstrate operability of the techniques described herein.

We previously introduced a method that we have called magnetic susceptibility magnitude imaging (SMI) that achieves mNP imaging with an array of drive coils, fluxgate magnetometers, and compensation coils. SMI scans localize and quantify mNPs with known alternating current (AC) magnetic susceptibility properties within the field of view of the system. We now propose enhanced hardware and methods that use the nonlinear magnetization response of mNPs to gain additional spatial information for SMI in a method we call nonlinear SMI (nSMI).

A magnetic nanoparticle imaging system has one or more driving coils driven at one or more frequencies, the driving coils positioned to provide magnetic fields and magnetic gradients to an imaging zone, and a static bias field magnet positioned to provide a static magnetic field with a bias and gradient to the imaging zone. One or more magnetic sensors are positioned to sense magnetic fields from the imaging zone, and a signal processor processes signals from the sensors to find at least signal magnitude of at least a second harmonic of the first frequency. In embodiments, the signal processing apparatus also determines signal intermodulation products of the first and second frequency, the intermodulation products further comprising at least a sum frequency of the first and second frequency. The signal processor maps the location of nanoparticles in the imaging zone based upon at least the magnitudes and phases of the harmonics of the first frequency and in embodiments where a second frequency is present, the magnitudes and phases of the intermodulation products.

Theory

Magnetic susceptibility imaging relies on the inherent magnetic susceptibility of mNPs to provide imaging contrast. When a magnetically susceptible material is subjected to an external magnetic field H, the resulting magnetic field will be $B=\mu_0(H+M)$, where $\mu_0$ is the magnetic permeability in a vacuum, B is the magnetic induction or B-field, H is the externally applied magnetic field strength, and M is the magnetization field from the magnetic material. The magnetization field arises from the magnetically susceptible material as $M=H\chi_v$, where $\chi_v$ is the volume magnetic susceptibility. In an AC magnetic field, the susceptibility is frequency dependent and has an in-phase and an out-ofphase component. For large mNPs in solution, like the ones we used, AC susceptibility can be modeled as Brownian relaxation.

Although the M-field only exists inside of the magnetic material, it gives rise to additional external B-field that contributes to the magnetic field detectable by a sensor outside the material. In magnetic saturation methods, the applied magnetic field becomes strong enough that the magnetization resulting from the applied magnetic field is no longer linear. The nonlinear magnetization M as a function of H is typically modeled with a Langevin function $$L(x) = \coth(x) - \frac{1}{x}. \quad (1)$$

Regardless of choice of nonlinear function, a Taylor series expansion of the Langevin function $$L(x) = \frac{1}{3}x - \frac{1}{45}x^3 + \ldots \quad (2)$$

can be used to approximate the magnetization in the nonlinear saturation regime. The applied magnetic field can then be substituted into the Taylor series to model the susceptibility at AC frequencies.

The nonlinear AC susceptibility response of mNPs varies spatially if there are magnetic strength field differences throughout an imaging volume.

In this study we propose a method to use the nonlinear magnetization response of mNPs to gain additional spatial information for SMI. We will first demonstrate how to use the magnetization at harmonic frequencies from a single drive coil to improve SMI. We demonstrate how detection of intermodulation frequencies, resulting from two magnetic fields at different frequencies, can also be used to improve SMI. Combining these two effects we demonstrate that the effects can be combined to obtain an additional improvement in SMI resolution.

Next, five time-multiplexed methods are presented to demonstrate that imaging resolution can be further improved without changing the coil and sensor configuration. The first method shifts the phase of the current in one of the drive coils while keeping the phase of the other drive coil constant. The second method scales the amplitude of the current in one or both drive coils. The third method shifts the phase of the current at two different frequencies in one of the drive coils while the phase of the other drive coil remains constant; the phase encoding scheme is used to obtain spatial information above and beyond what can be obtained from the harmonic and intermodulation frequencies alone The fourth method synchronously shifts the phase in both drive coils. Finally, the fifth method varies the frequency of the AC current in the drive coils. These methods rely on the nonlinear magnetization of mNPs and are used to further improve the spatial resolution of nSMI.

Methods

Analog and Digital Systems

A proof-of-concept experimental setup 100 (FIG. 1) has a frame 102 with two drive coils 104, 106 and a sense coil 107. The drive coils (Jantzen-1257, 0.3 mm diameter wire, 7 mH, 11.8Ω at DC, 15 mm inner diameter×15 mm height×26 mm outer diameter, Jantzen, Praestoe, Denmark) were arranged orthogonally to the sense coil 107 (Jantzen-1257). All three coils were positioned around a 3×6 imaging grid 108 where nanoparticle-containing samples can be placed 5 millimeters apart, with a 2.5 mm separation between the drive coils and a 2.5 mm separation between the sense coil and the edge of the drive coils. Drive coils 104, 106 are driven by appropriate coil drivers 120, such that the current in the coils depended on the testing frequency but was between 150-200 mA, producing magnetic fields of around 5 millitesla (mT) in the center of the coil. A DC magnetic field was also added by positioning eight neodymium permanent magnets 121 positioned 50 mm from the back of the grid, in plane with the drive coils as illustrated. The permanent magnets are placed in a magnetically permeable frame, not shown, arranged such that a magnetic gradient 109 exists across the array, with some (left samples in FIG. 1) sample positions of imaging grid 108 subjected to a higher static field than other (right samples in FIG. 1) sample positions of imaging grid 108.

Sense coil 107 is coupled through sensor electronics 122 to data acquisition and control electronics 124, which also controls coil drivers 120.

In a single frequency per coil mode, each coil is driven at a separate frequency, the first coil 104 at a first frequency F1, and the second coil at a second frequency F2.

In a dual-frequency per coil mode, each coil is driven with superimposed sine waves at two, or more, different frequencies thereby allowing nonlinear responses of magnetic nanoparticles to generate intermodulation products. In an embodiment each coil is driven with the same two frequencies, in this embodiment location sensing can be achieved through phase encoding. In another embodiment at least one of the two frequencies is different for each coil, in this embodiment location sensing can be achieved both through phase encoding and through relative magnitudes of differing intermodulation products.

Data acquisition and control electronics 124 operates under control of a processor 126, and provides amplified and digitized signals received from the sense coil 107 to processor 126. In an embodiment, processor 126 has a program memory 128 having recorded therein reconstruction code 130 that incorporates lock-in amplifier code associated with each frequency at which the coils are driven and harmonics thereof, and at each intermodulation product frequency expected to be found in signals from the sense coils. In an alternative embodiment, processor 126 has a program memory 128 having recorded therein reconstruction code 130 that includes fast-Fourier transform (FFT) code for determining strength and phase of harmonics of the drive frequencies F1 and F2, as well as strength and phase of intermodulation frequencies such as sum and difference frequencies between F1, F2, and harmonics of F1 and F2. In an embodiment the lock-in amplifier code or FFT code can provide information of components of signal from coil 107 at at least F1, F2, F1+F2, F1−F2, F1+2F2, F1−2F2, F1+3F2, F1−3F2, 2F1+F2, 2F1−F2, 3F1+F2, 3F1−F2, 2F1+2F2, 2F1−2F2, 2F1, 3F1, 4F1, 2F2, 3F2, and 4F2. In an embodiment, the presence of a static magnetic field gradient from a first (left) side to a second (right) side of the array 108 causes a shift in a ratio of odd to even harmonics from nanoparticles positioned on the first side to nanoparticles positioned on the second side of the array.

In alternative embodiments, where a first driving coils is driven at two frequencies F1 and F2, and a second driving coil is driven at two frequencies F1 and F3, the lock-in amplifier code or FFT code is configured to provide information of components of signals from coil 107 including F1, F2, F3, F1+F2, F1−F2, F1+F3, F1−F3, F2+F3, F2−F3, 2F1, 2F2, 2F3, 2F1+F2, 2F2+F3, 2F3+F1, F1+F2+F3, F1−F2+

F3, F1+F2−F3, F1−F2−F3, and similar harmonic and intermodulation product frequencies.

In order to avoid eddy currents, in a particular embodiment each driven frequency is less than 10 kHz.

Second Proof of Concept System

Figure 1A:
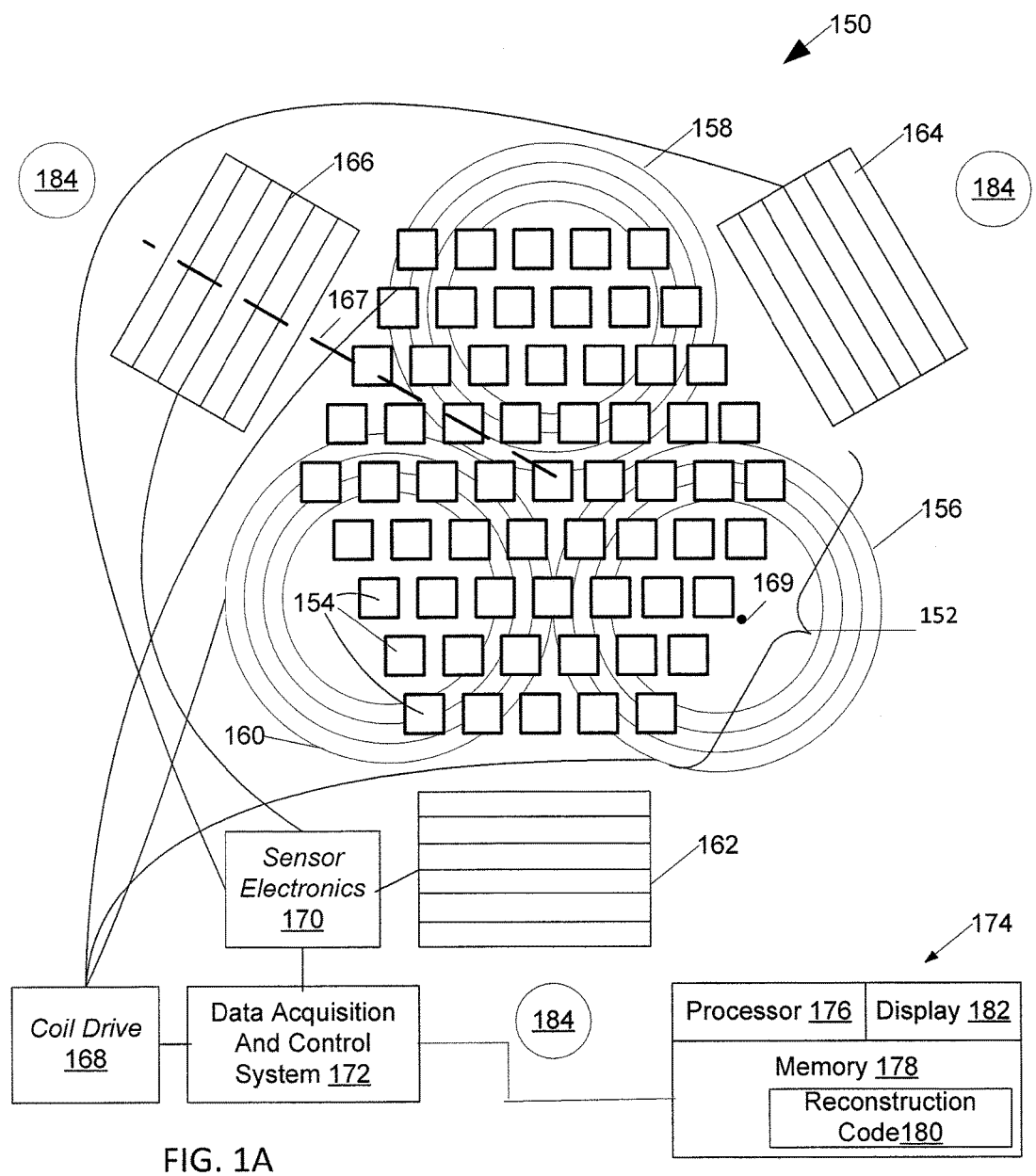
FIG. 1A is a block schematic illustration of a second experimental apparatus used to demonstrate operability of the techniques described herein.

A second proof of concept experiment 150, FIG. 1A, has an imaging grid 152 having a hexagonal array of 61 voxels 154. The grid was removable, with 5-mm spacing and cylindrical wells of 3.5 mm diameter and 4.2 mm in height. The experiment is equipped with three driving coils 156, 158, 160 located under grid 152, and three sensor coils 162, 164, 166 located at three sides of grid 152 and oriented perpendicularly to driving coils 156, 158, 160. Sensor coils 162, 164, 166 each have an axis, such as axis 167, that is perpendicular to an axis of each driving coils 156, 158, 160. In the figure, each driving coil 156, 158, 160 has an axis, such as axis 169, that is parallel to the axes of the other driving coils and is perpendicular to the page in FIG. 1A. Driving coils 156, 158, 160 are driven by coil drivers 168, and sensor coils 162, 164, 166 feed through sensor electronics 170 are measured by data acquisition and control subsystem 172. To achieve higher currents than in previous studies, a resonant circuit for the coil drivers 168 was constructed for each of the driving or excitation coils 156, 158, 160 using capacitors of 20 μF and tuned to two frequencies (327 and 350 Hz). This arrangement allowed for multiple frequencies to be present on each excitation coil. In a particular experiment, the electric current in each of the excitation coils was approximately 600 mA peak-to-peak and produced magnetic fields of approximately 10 mT in the center of the excitation coils. DC magnetic field gradient was also created by positioning 3 vertical stacks of 4 neodymium permanent magnets located 3.5 cm from the imaging zone and 1 neodymium magnet positioned in plane with each detection coil.

Measurements of signals at sensor coils 162, 164, 166 performed by data acquisition and control subsystem 172 are fed to and processed by a signal processing subsystem 174 having a processor 176 coupled to a memory 178, the memory having a reconstruction firmware 180 and display firmware (not shown). Reconstructed images are displayed on a display subsystem 182. In an embodiment, small permanent magnets 184 are provided to provide a DC or static magnetic bias field, which in a particular embodiment incorporates a magnetic field gradient through an imaging volume occupied by the grid.

Sensor electronics 170 of the second proof of concept system 150 is sensitive to phase of recovered intermodulation products and harmonics, as well as to amplitude. System 150 is therefore adapted to phase encoded operation in which each excitation coil has the same set of frequencies that can be phase offset from each other.

Testing was performed for the second proof of concept system 150 using Fe3O4 starch coated mNPs with a hydrodynamic diameter of 100 nm (10-00-102, micromod Partikeltechnologie GmbH, Rostock, Germany). All samples were at a concentration of 25 mg/ml. A volume of 40 μL of mNP solution was pipetted into the cylindrical wells at desired locations. Lids of 1.5 mm thick acrylic were epoxied onto the imaging grids to provide a waterproof seal. Fourteen imaging grids with differing patterns were created and MNP samples were pipetted into 11 locations for calibration and several spatial patterns for imaging experiments.

To achieve higher resolution than possible with the harmonic and intermodulation data collected from the sense coils, a phase encoding scheme was implemented to provide additional measurements. To achieve this encoding scheme each of the three excitation coils were driven at the same two frequencies but with different phase offsets. The phase encoding scheme used four phase rotations with different phases for each frequency. The two frequencies have an initial π/2 phase shift such that the magnetic field spatial patterns are well separated and do not mirror one other. The applied magnetic fields used are capable of producing a susceptibility response from the mNPs that contains the 2nd and 3rd harmonics, as well as the 2nd and 3rd intermodulation frequencies. When measured with 3 detection coils, this produces 27 data channels per phase setting, and so by using 4 phase rotations we can capture 108 data channels. By splitting the measurements into in-phase and out-of-phase measurements, the number of data channels doubles to 216. These 216 data channels are then used to create 61-voxel nSMIs.

TABLE 1

Phases used with same-frequency, phase-encoded experiments

| Excitation Coil | Phase Rotation | | | |
| --- | --- | --- | --- | --- |
| | 1 | 2 | 3 | 4 |
| 1 | 0, π/2 | 0, π/2 | 0, π/2 | 0, 0 |
| 2 | 0, π/2 | 0, 0 | 2π/3, π/2 | 2π/3, π/2 |
| 3 | 0, π/2 | 2π/3, π/2 | 2π/3, 0 | 0, π/2 |

Initially, a calibration was performed by splitting the imaging grid into regions of 10 grid locations (minus the center point) that each comprise ⅙th of the imaging grid. A calibration sample was created for each of these 10 grid locations containing an mNP sample. The calibration data was obtained by measuring the response to the calibration sample at each of the 4 phase rotations before reorienting the calibration sample through the remaining 5 orientations that make up a full set of placements around the hexagonal imaging grid.

Once all 61 calibration points were measured, a calibration matrix was constructed according to the method described above with respect to the first proof of concept system. With the calibration matrix fully constructed, nSMIs were obtained from mNP samples arranged into hexagonal and bar patterns. In addition, a hexagonal saline pattern was also imaged as a control. The images were reconstructed using a non-negative least squares function (lsqnonneg) in Matlab (The MathWorks Inc., Natick, Mass., USA) executing on image processor 176.

In an alternative embodiment we anticipate automating the calibration process, using an electromechanical positioning device to position calibration samples at raster-based calibration locations that are more closely spaced than the 61 sampling points of the proof-of-concept grid; it is anticipated we may also perform a one-time initial calibration with smaller samples, and sample positions that overlap in a dense raster, such that future embodiments will produce continuous images rather than the coarse grids of our experiments. It is expected that the system is capable of greater resolution than has been demonstrated so far with the existing sample grids.

In an alternative embodiment, a voxel-based forward model of the system is developed, with parameters for magnetic nanoparticle concentration at each voxel. In this embodiment, nSMIs are obtained by obtaining readings of phase and intermodulation products, then fitting the concentration parameters to determine concentration at each voxel.

Figure 1B:
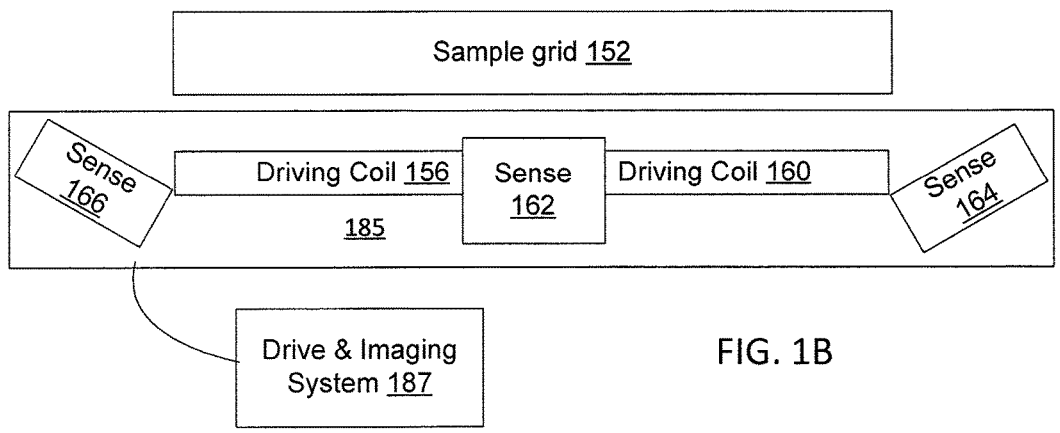
FIG. 1B is a schematic side view of a system having a handheld imaging wand or head that may be placed on tissue, and adapted for imaging magnetic nanoparticle concentrations within the tissue.

It has been found that the sense coils need not be oriented perpendicular to the drive coils. In an embodiment, as illustrated in FIG. 1B, the driving coils 156, 160, sensing coils 162, 164, 166, and permanent magnets (not shown) are integrated into portable sensing head 185 that may in an embodiment be handheld. The sensing head 185 is coupled by a cable to an imaging system 187 that contains the coil drivers, sensor electronics, data acquisition system, processor, memory, and display system described with reference to FIG. 1A. In a particular embodiment, the permanent magnets are omitted and a DC current is superimposed on the AC currents heretofore described as provided to driving coils 156, 158, 160 to provide a DC bias magnetic field.

In both proof of concept systems, there is no field-free point (FFP) or unsaturated zone surrounded by zones with intense fields where nanoparticles would be magnetically saturated as found in conventional magnetic nanoparticle imaging systems. The magnetic fields within the imaging zone are insufficiently strong to maintain magnetic particles in magnetic saturation for a period in excess of a cycle of the first AC driving circuits.

Full Scale Systems

It is expected that the proof of concept experiments will scale to a full-size imaging machine 200. In machine 200, a main magnet with poles 202 provides a static or DC magnetic bias field, within which a subject and/or tissue 204 may be placed. Tissue 204 may have one or more concentrations 205 of nanoparticles. While a C-shaped magnet is illustrated the main magnet may have other forms; the magnet provides a field oriented along a first axis 222.

In an embodiment, nanoparticle concentrations 205 arise in tissue 204 through administration of nanoparticles to the subject, in some embodiments these nanoparticles are administered through particular vessels such that they concentrate in particular organs, in other embodiments the nanoparticles are tagged with a tissue-selective coating, such as a coating containing a tumor-sensitive antibody. The nanoparticles in some embodiments are administered as a contrast agent for localizing particular tissue types, and in other embodiments are administered because nanoparticle concentrations may be heated by applying strong AC fields and thereby apply thermotherapy to tissues in which they become concentrated—in both cases it is desirable to map nanoparticle concentrations 205. It is expected also that, when magnetic nanoparticles having a tissue-selective binding agent are used, those particles will have sufficiently different response between their bound and unbound states to permit in an embodiment selective imaging of bound nanoparticles; this embodiment is expected to better distinguish tumor than other embodiments.

It is known that responses of magnetic nanoparticles to imaging systems vary with temperature. In an embodiment we take advantage of this attribute of nanoparticles to map temperature of tissue along with mapping magnetic nanoparticle concentrations. In a particular embodiment, the map of tissue temperature obtained from the magnetic nanoparticles is used to monitor and control thermotherapy. Indeed, in an embodiment the driving coils 156, 158, 160 double as coils for providing AC magnetic fields for heating magnetic nanoparticles during performance of thermotherapy.

Figure 2:
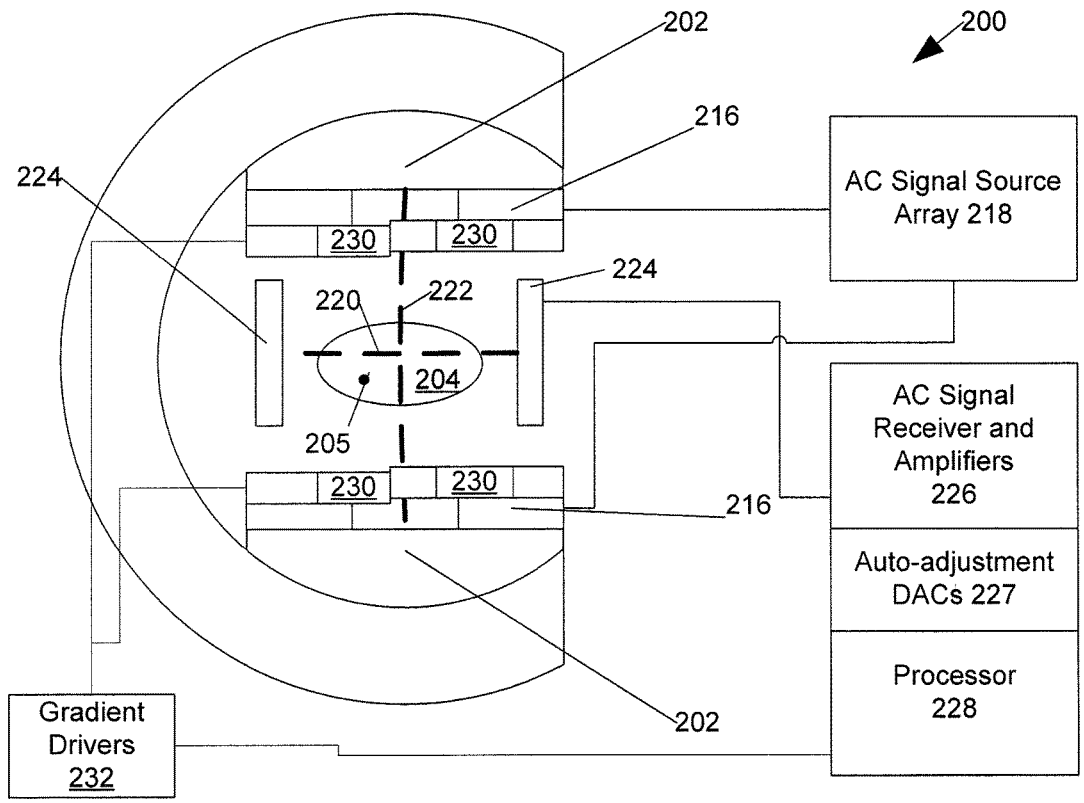
FIG. 2 is a block diagram of a larger medical imaging system based on the techniques described herein, and having driving coils located along two (top and bottom) sides of the imaging zone.
Figure 2A:
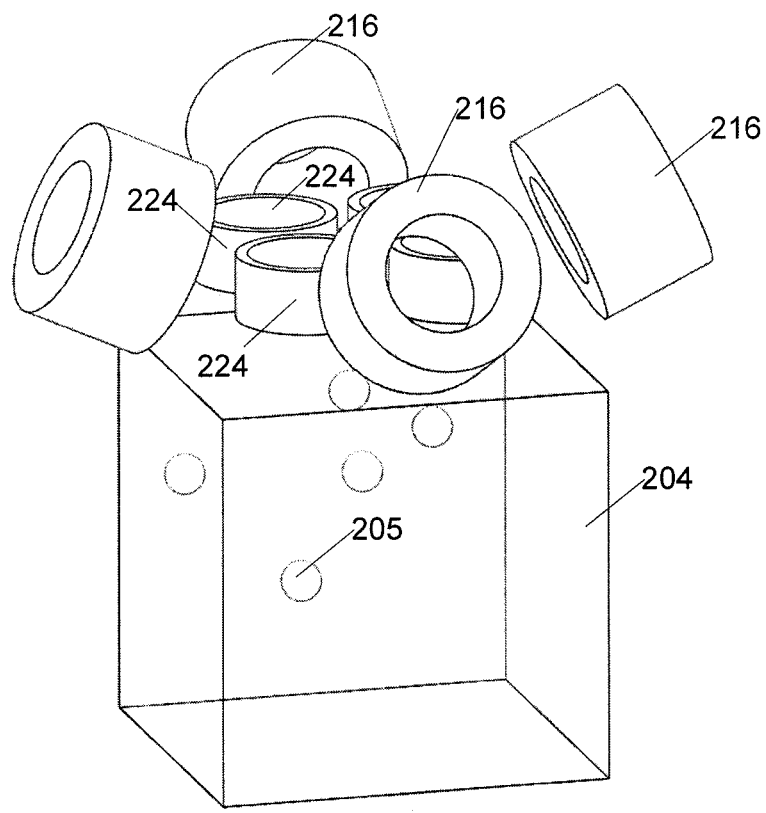
FIG. 2A is a schematic diagram illustrating non-perpendicular driving and sensing coils along one side of an imaging zone.
Figure 2B:
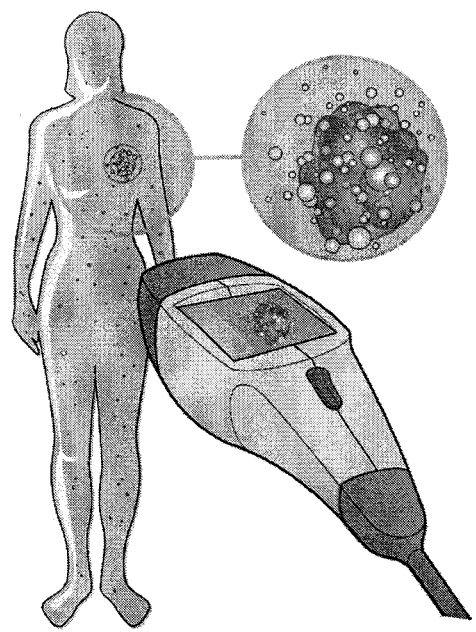
FIG. 2B illustrates a handheld probe implementation of the present invention.

Imaging device 200 also includes not merely a single AC magnetic driving coil, but a planar array 216 each having many AC magnetic driving coils with each AC magnetic drive coil creating a magnetic gradient across the imaging zone, the coils driven separately by an AC signal source of a signal source array 218; the signal source array 218 being capable of driving each driven coil at a different frequency to permit nonlinear signal mixing, such that intermodulation-frequency signals can form. The driving coils 216 are arranged to provide an AC magnetic field gradient along axis 222. Also provided are two opposed arrays 224 of sensors, in an embodiment these are sensing coils, in alternative embodiments other types of sensors such as Hall-effect sensors are used or sensing coils arranged as gradiometers. Sensor arrays 224 are oriented to sense magnetic fields along an axis 220 perpendicular to the axis 222 between poles 202 of the main magnet and passing through the imaging zone. While sensing fields along a perpendicular axis has the advantage of minimizing signal picked up directly from driving fields at fundamental frequency, in other embodiments, as illustrated in FIG. 2A, driving and sensing coils are oriented at non-perpendicular angles and may be located on only one side of the imaging zone, these systems may in some embodiments have a handheld imaging head that may be applied to skin of a subject to provide two, or in some embodiments three, dimensional maps of magnetic nanoparticles beneath skin of the subject. In other embodiments, the magnetic field sensors are gradiometers positioned to be insensitive to the magnetic fields from the AC drive coils. Sensing arrays 224 are configured to sense changes in magnetic fields within the imaging zone along the axis 222 between pole pieces 202, and are provided for sensing signals, produced by interactions of the AC magnetic field along axis 220 with magnetic nanoparticles in subject and/or tissue 204. Each sensor of sensor arrays 224 are coupled to signal receiver and sense amplifier electronics 226; sense amplifier electronics is coupled to processor 228 which is configured to perform spectral analysis and image reconstruction based upon signals from coils 224. Sense amplifier electronics 226 and processor 228 together form a signal processing subsystem for determining a response from signals form coils 224.

In an alternative embodiment, the driving and sensing coils for any particular collection of imaging data are determined at run-time from a pool of dual-purpose coils. In this embodiment, an individual coil serves as a driving coil with neighboring coils serving as sensing coils while obtaining a first data set, and that individual coil then serves as a sensing coil while one or more nearby coils serves as driving coils while obtaining a second data set. Image reconstruction then uses both the first and second data sets to determine a map of magnetic nanoparticle concentrations in a subject.

In an embodiment, since static magnetic fields help localize nanoparticle concentrations because harmonics and intermodulation products change with field strength, coils 230 and associated coil drivers 232 are provided near one or both pole pieces to provide a static field. Static coil drivers 232 operate under control of processor 228. In an alternative embodiment, static magnet coils 230 are omitted and permanent magnets are used. In another alternative embodiment, a small DC current is superimposed upon the driving coils 216 to provide a static magnetic field and magnetic field gradients.

Static field for the purposes of this document means a magnetic field component that either remains constant during imaging, or is changed slowly relative to the AC field; for example the term includes systems where a bias field having a gradient along one axis of a subject while harmonics of an applied AC field are measured, and then switched to having a gradient along a different axis of the subject while harmonics of an applied AC field are again measured. In this way, DC gradients can be used as an encoding scheme to acquire additional data for imaging. Since static magnetic fields may be provided by an electromagnet, such as coils 230, or by permanent magnets, or by combinations of electromagnets and permanent magnets; and shifts in static gradients may be achieved by adjusting currents in coils 230 or by mechanically rotating or shifting permanent magnets or pole pieces, the term "static magnet" as used herein shall include any arrangement of electromagnet(s) and/or permanent magnet(s) configured to provide a static field as described in this paragraph.

In several embodiments herein described there may be sufficient current in drive current coils and/or gradient coils to produce heating of those coils. In these embodiments, a thermoelectric cooler and a coolant circulation system is provided to limit temperature rise of the coils. Since heating of driving coils and sensing coils can change the electrical resistance of the coils causing altered readings, in an embodiment, coil temperatures are monitored and regulated with a thermal regulation system. In this embodiment, the driving coils are operated continuously until they reach a preferred operating temperature, and, once they have reached the preferred operating temperature, they are maintained at their preferred operating temperature by variation of the amount of cooling that is applied to the coils. In another embodiment, the current in the driving coils is regulated to maintain constant magnetic field levels despite thermal changes in the coil resistance. This current regulation system allows for the preferred operating temperature to be a range rather than a fixed point. In an embodiment, the temperature of the sensing coils is monitored and, with a known correlation with the coil resistance, used to apply a correction factor to the sensed field so that readings remain accurate within a preferred operating temperature range.

Nanoparticles

Testing was performed using $Fe_3O_4$ starch coated mNPs with a hydrodynamic diameter of 100 nanometers (nm). Two samples of these mNPs were prepared. The first was a full concentration sample (25 mg Fe/ml) and the second sample was diluted to 12.5 mg Fe/ml. Both samples were placed in 0.5 ml tubes for use in the array of FIG. 1, where each voxel of the array could accept one tube. Similarly, patterns of sample wells in the 61-voxel grid of FIG. 1A were filled with 40 μl volumes of Fe3O4 starch coated magnetic nanoparticles (mNPs) with a hydrodynamic diameter of 100 nm and a concentration of 25 mg/ml. Throughout this document, a magnetic nanoparticle is a particle of average diameter size between 5 nanometers and 250 nanometers. In alternative embodiments, magnetic microparticles having average diameter of between 250 nanometers and 2500 nanometers are used instead of magnetic nanoparticles of less than one quarter micron in size.

Model and Imaging

Figure 3:
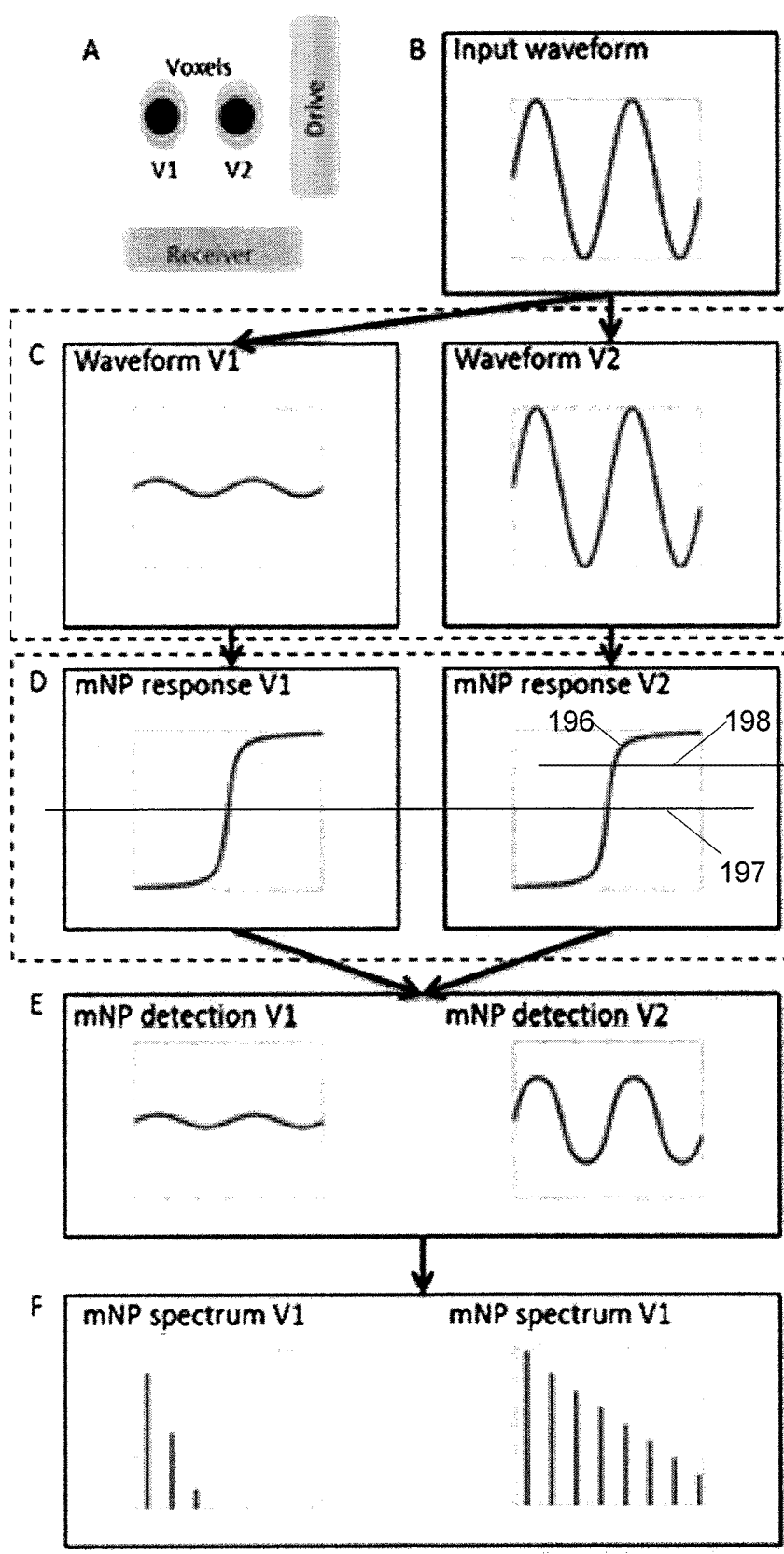
FIG. 3 illustrates principles of the system for a single coil and sensor, and is divided into sections A, B, C, D, E, and F. Section A depicts the experimental apparatus with a single drive coil, sensor and two imaging voxels having mNP samples. Section B illustrates an input waveform to the drive coil. Section C illustrates the applied magnetic field at each voxel, with voxel V2 having a larger applied magnetic field due to its closer proximity to the drive coil. Section D illustrates nonlinear mNP response to the applied magnetic field. Section E illustrates signals received by sensing coils from the mNPs in both voxels. Section F illustrates a detected frequency spectrum for each voxels. The spectrums are different, leading to spatial information about the mNP concentrations in the voxels.

A simplified model is developed here to show the mathematical principles of nSMI. An illustration of this simplified model of nSMI is shown in FIG. 3. In this model, it is assumed that the imaging system contains one drive coil, one sensor coil, and two imaging voxels. As illustrated, the interactions of the applied field with the nonlinear magnetization of the mNPs gives rise to spatially varying harmonic amplitudes that can be used to resolve signals from differing voxels in nSMI. We model AC magnetic fields of the form $$H_{DV_n} = G_{DV_n}(A'' \sin(\omega_0 t + \varphi_0) + A' \cos(\omega_0 t + \varphi_0)), \quad (3)$$

where $G_{DV_n}$ is a geometric factor between the drive coil and voxel, the A coefficients are user-specified electronic gains, $\omega_0$ is the drive coil frequency, and $\varphi_0$ is an unknown but constant phase lag from the system hardware. The magnetic field in the nth voxel is $$B_{DV_n} = \mu_0(H_{DV_n} + M_{DV_n}), \quad (4)$$

where the magnetization of the voxel from the drive coil field is assumed to follow a Langevin function of equation 1 applied to the mNPs $$M_{DV_n} = [mNP]_n m_n \left[\coth\left(\frac{m_n H_{DV_n}}{k_B T}\right) - \frac{k_B T}{m_n H_{DV_n}}\right], \quad (5)$$

where T is the temperature, $k_B$ is Boltzmann's constant, $[mNP]_n$ is the concentration of is mNPs, and $m_n$ is the magnetic moment of the nth voxel. The magnetic moment $m_n = \frac{1}{6}\pi D_n^3 M_{sn}$, where D is the diameter and $M_{sn}$ the magnetic saturation of the mNPs in the nth voxel. A simplified version of the Langevin model may be obtained with a Taylor series expansion (equation 2), which is proportional to the mNP concentration in the voxel and the lumped parameter coefficients $\beta_1$ and $\beta_3$ $$M_{DV_n} = [mNP]_n(\beta_1 H_{DV_n} + \beta_3 H_{DV_n}^3). \quad (6)$$

The magnetic field measured by sensor S due to the magnetization of the nth voxel is $$B_{DV_nS} = G_{V_nS} V_n \mu_0 M_{DV_n}, \quad (7)$$

where $G_{V_nS}$ is a geometric factor from the voxel to the sensor and $V_n$ is the volume of the voxel. Expanding the sensor measurement expression we obtain $$B_{DV_nS} = G_{V_nS} V_n \mu_0 [mNP]_n \quad (8)$$
$$\left\{\left[\frac{3\beta_3 G_{DV_n}^3}{4}(A'^2 A'' + A''^3) + \beta_1 G_{DV_n} A''\right]\sin(\omega t + \phi_0 + \phi_1) + \right.$$
$$\left[\frac{3\beta_3 G_{DV_n}^3}{4}(A' A''^2 + A'^3) + \beta_1 G_{DV_n} A'\right]\cos(\omega t + \phi_0 + \phi_1) +$$
$$\frac{3\beta_3 G_{DV_n}^3}{4}(A'^2 A'' - A''^3)\sin(3\omega t + \phi_0 + \phi_3) +$$
$$\left.\frac{3\beta_3 G_{DV_n}^3}{4}(A'^3 - A' A''^2)\cos(3\omega t + \phi_0 + \phi_3)\right\},$$

where $\varphi_1$ and $\varphi_3$ are additional unknown but constant phase lags due to sensor electronics and the frequency-dependent complex susceptibility response of the magnetic material. Using reference sinusoids $$R'_1 = \cos(\omega t),$$

$$R''_1 = \sin(\omega t),$$

$$R'_3 = \cos(3\omega t),$$

$$R''_3 = \sin(3\omega t), \quad (9)$$

multiplying the sensor measurement by each of the references and taking a time average, the signals converge to $$\overline{B_{DV_nS} R'_1} = G_{V_nS} V_n \mu_0 [mNP]_n \quad (10)$$
$$\left\{\left[\frac{3\beta_3 G_{DV_n}^3}{4}(A'^2 A'' + A''^3) + \beta_1 G_{DV_n} A''\right]\sin(\phi_0 + \phi_1) + \right.$$
$$\left.\left[\frac{3\beta_3 G_{DV_n}^3}{4}(A' A''^2 + A'^3) + \beta_1 G_{DV_n} A'\right]\cos(\phi_0 + \phi_1)\right\},$$

-continued $$\overline{B_{DV_n}sR_1''} = G_{V_n}sV_n\mu_0[mNP]_n \tag{11}$$
$$\left\{\left[\frac{3\beta_3 G_{DV_n}^3}{4}(A'^2A'' + A''^3) + \beta_1 G_{DV_n}A''\right]\cos(\phi_0 + \phi_1) - \right.$$
$$\left.\left[\frac{3\beta_3 G_{DV_n}^3}{4}(A'A''^2 + A'^3) + \beta_1 G_{DV_n}A'\right]\sin(\phi_0 + \phi_1)\right\},$$

$$\overline{B_{DV_n}sR_3'} = G_{V_n}sV_n\mu_0[mNP]_n\left\{\frac{3\beta_3 G_{DV_n}^3}{4}(A'^2A'' - A''^3)\sin(\phi_0 + \phi_3) + \right. \tag{12}$$
$$\left.\frac{3\beta_3 G_{DV_n}^3}{4}(A'^3 - A'A''^2)\cos(\phi_0 + \phi_3)\right\},$$

$$\overline{B_{DV_n}sR_3''} = G_{V_n}sV_n\mu_0[mNP]_n\left\{\frac{3\beta_3 G_{DV_n}^3}{4}(A'^2A'' - A''^3)\cos(\phi_0 + \phi_3) - \right. \tag{13}$$
$$\left.\frac{3\beta_3 G_{DV_n}^3}{4}(A'^3 - A'A''^2)\sin(\phi_0 + \phi_3)\right\}.$$

Assuming we have 2 only voxels and one harmonic response, these equations can be arranged into a matrix form $$\begin{bmatrix}\overline{B_{DVS}R_1'}\\ \overline{B_{DVS}R_1''}\\ \overline{B_{DVS}R_3'}\\ \overline{B_{DVS}R_3''}\end{bmatrix} = \mu_0 V_n \begin{bmatrix}G_{V_1}sK'_{1V_1} & G_{V_2}sK'_{1V_2}\\ G_{V_1}sK''_{1V_1} & G_{V_2}sK''_{1V_2}\\ G_{V_1}sK'_{3V_1} & G_{V_2}sK'_{3V_2}\\ G_{V_1}sK''_{3V_1} & G_{V_2}sK''_{3V_2}\end{bmatrix}\begin{bmatrix}[mNP]_1\\ [mNP]_2\end{bmatrix} \tag{14}$$

where the K' constants represent all of the terms inside the curly brackets of the in-phase amplitudes of equations (10) and (12) and the K" constants represent all of the terms inside the curly brackets of the out-of-phase amplitudes of equations (11) and (13). Equation (14) allows for the simultaneous solution of the mNP concentrations in voxels 1 and 2 from the measurements made by a single drive coil and single sensor as illustrated qualitatively in FIG. 3.

It should be noted that presence of a static magnetic field shifts an operating point of nanoparticles from a baseline 197 (FIG. 3, part D) to an operating point 198 this shift causes differences in harmonics generated as the applied AC fields sweep the nanoparticles through the nonlinear 196 regions of operation. A DC gradient field acts similar to an AC gradient field and will cause a spatial difference in the generation of harmonic fields as the result of an applied AC magnetic field.

The forward model given above can be obtained empirically from a calibration data set without any prior knowledge of the mNP properties as was done in. This approach to nSMI can also be extended to the case where intermodulation frequencies are created or when a direct current (DC) magnetic field is applied and can be extended to any size of imaging zone, including a 3-dimensional zone.

Experimental Setup

To demonstrate nSMI using the additional spatial information obtained from nonlinear interactions between the applied magnetic field and mNPs, an experiment was conducted using the apparatus described above with reference to FIG. 1. Several data analysis streams where then used to demonstrate spatial encoding using each of the nonlinear effects outlined in the introduction. Initially, a calibration was run by placing the 25 mg Fe/ml sample successively into each of the voxel locations for a period of time. The calibration matrix was then constructed according to equation (14). Once the calibration was complete, the 25 mg Fe/ml sample was re-tested in each of the voxel locations. SMI was first performed only using data from the primary signal and harmonics of drive coil 1, then the primary signal and harmonics of drive coil 2 and finally from both the primary signals and all intermodulation frequencies. SMIs were constructed with 1 to 12 voxels and $R^2$ values were computed for each image. Given the limited number of harmonic fields and intermodulation frequencies, the SMIs are expected to have high $R^2$ values for small numbers of voxels and poor $R^2$ values for higher numbers of voxels.

To demonstrate tomographic imaging, nSMI was performed with the 25 mg Fe/ml and 12.5 mg/ml nMP samples located simultaneously in the imaging grid. Imaging was performed by placing each sample in the grid and moving one sample to a new location every 20 s. Due to the size of the Eppendorf tubes, it was not possible to place the samples in immediately adjacent positions. All SMIs were reconstructed using a noise-weighted non-negative least squares (lsqnonneg) function in Matlab (The MathWorks Inc., Natick, Mass., USA).

Figures 4, 4A:
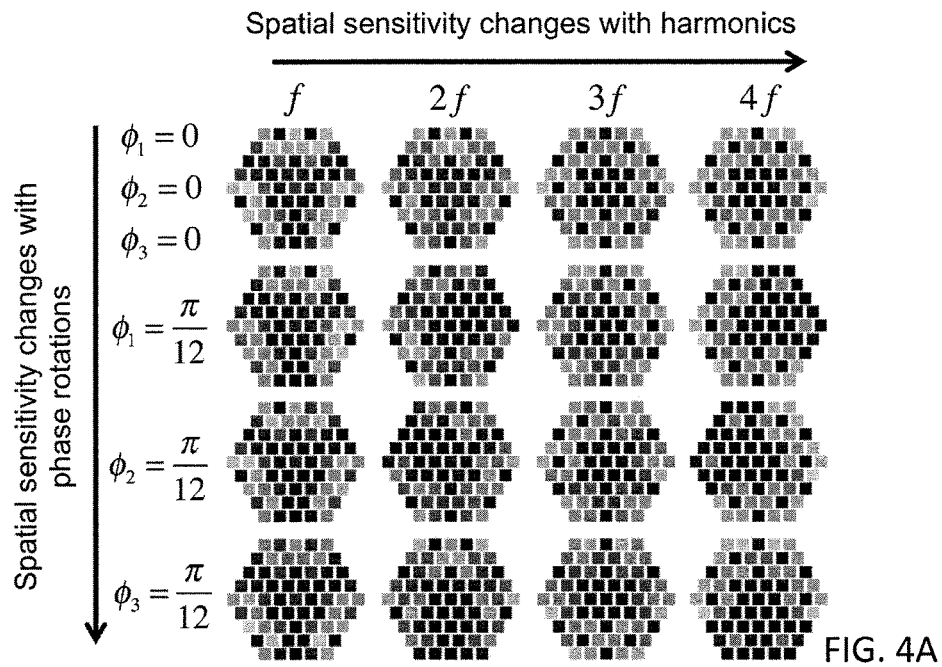
FIG. 4 illustrates principles of extended phase-dependent resolution methods, as described herein.
FIG. 4A illustrates phase resolution and per-voxel sensitivities obtained with the second proof of concept system.

During testing it was noted that there was a difference between the spatial information contained in the in-phase and the out-of-phase imaging data. This led to an investigation into methods that might lead to additional spatial information beyond the use of harmonic and intermodulation frequencies for SMI. These methods could be used as encoding methods and combined with harmonic and intermodulation data to produce images. Five methods and one control method were tested. These methods are illustrated in FIG. 4 and include:

B. asynchronous phase modulation of driving signals or asynchronous time multiplexing between discrete phases,
C. amplitude modulation, or time multiplexing between discrete amplitudes,
D. synchronous phase modulation or synchronous time multiplexing between discrete phases,
E. intermodulation asynchronous phase modulation, or intermodulation asynchronous time multiplexing between discrete phases and
F. frequency modulation, or time multiplexing between discrete frequencies.

In each method, one parameter was varied over four conditions and the data from each condition was aggregated to reconstruct nSMI. Testing was performed by placing the 25 mg Fe/ml sample in each of several voxel positions and then retesting under the same conditions. Once the test/retest was completed, the next condition was applied and the same procedure repeated. In each method, only the $3^{rd}$ harmonic frequency or the first intermodulation frequency was used for SMI reconstruction, in future embodiments other harmonics may also be used.

The control method A was a control using full amplitude and a 0° phase shift in each coil for each of the four conditions. In method B, the left coil was driven with a 0° phase shift while the right coil was given an incremental phase shift of 90° per condition. In method C, the amplitude of the right and left coils were varied to be either 100% or 75% of the maximum amplitude. In method D, the phase of the left and the right drive coil were incrementally shifted synchronously by 90° per condition. In method E, intermodulation frequencies were created by using two frequencies in each coil. The left coil was given a constant phase while the phase of the frequencies in the right coil was incrementally shifted by 90° per condition. Finally in method F, the frequency of the left and right coil was changed in each condition.

FIG. 4A illustrates the effect on the second experiment 150 (FIG. 1A) of phase encoding combined with harmonics and intermodulation to increase imaging resolution. A set of phase rotations between the three stimulus coils, as given on the vertical axis, where all coils were operating at the same frequency, was used and responses of nanoparticles in certain voxels were found to be more sensitive than others to position. Phase was rotated by changing the relative phase of stimulus coils, and responses of nanoparticles observed as illustrated in rows of FIG. 4. The voxels in which responses were more sensitive than others to position changes with the phase changes. Similarly, data was taken at different harmonics of the drive frequency as illustrated in columns of FIG. 4A. By obtaining data at multiple sets of phase rotations, and harmonic selections, we expect to be able to accurately determine positions of nanoparticles. It is expected that the voxels of the grid used in the proof of concept systems will correspond to voxels in systems configured to image nanoparticle concentrations in live subjects.

Results

Figure 5:
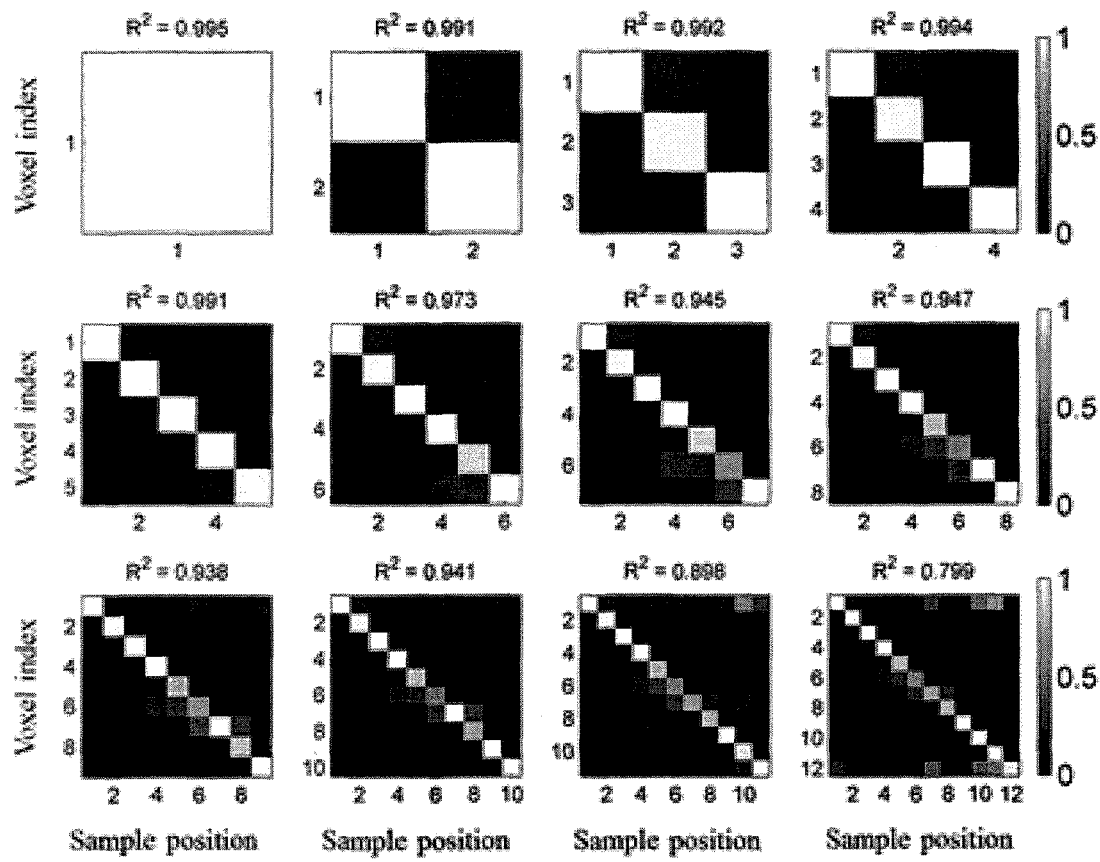
FIG. 5 illustrates harmonic signals observed, and voxel resolution, as a vial containing nanoparticles is moved through the voxel locations of the experiment of FIG. 1.
Figures 6, 7:
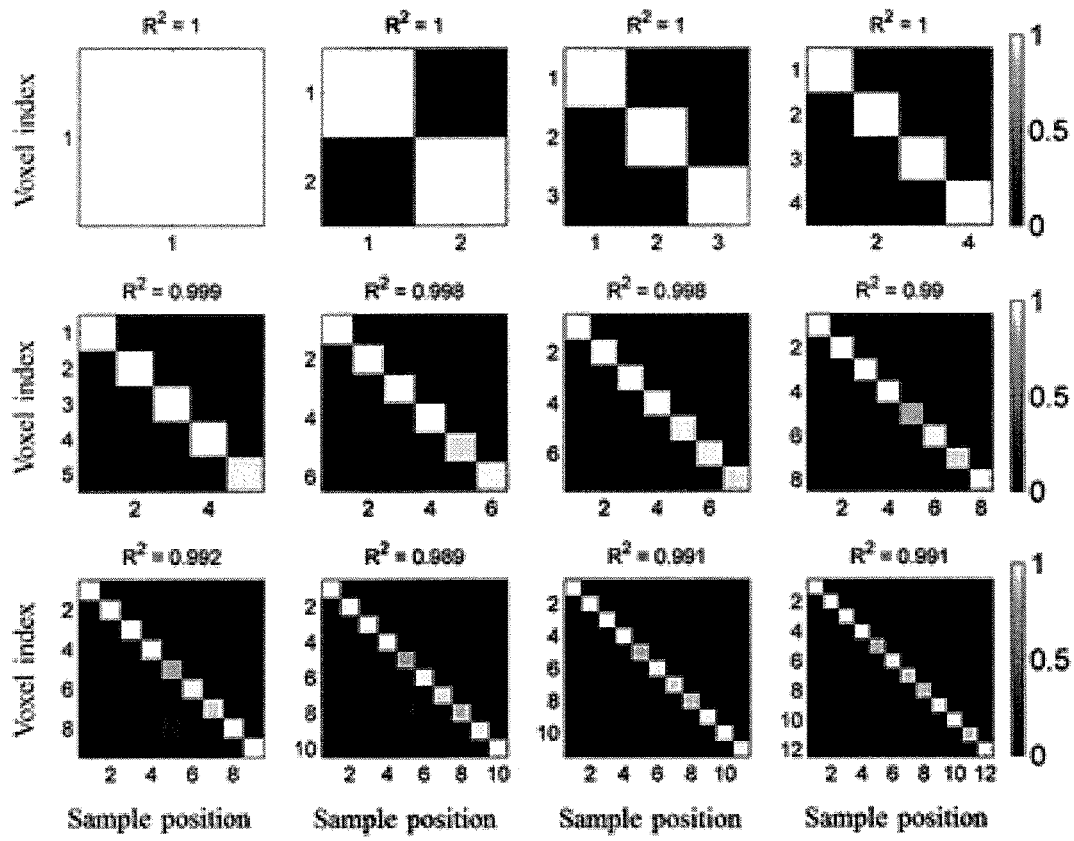
FIG. 6 illustrates intermodulation observed, and voxel resolution, as a vial containing nanoparticles is moved through voxel locations of the experiment.
FIG. 7 is a graph of $R^2$ statistics for image reconstruction with intermodulation frequencies and primary frequencies from two coils with $R^2$ values as a function of the number of reconstructed voxels for in-phase data, out-of-phase data, and combined data sets.

A demonstration of the use of nonlinear mNP magnetization to add spatial information to SMI is shown in FIGS. 5 and 6. In these figures, a voxel index is shown on the y-axis and an image is created at each x-axis position. The sample is being moved through the 3×4 grid at regular time intervals and images are being reconstructed at each sample position. The expected outcome is a 1 (shown as grey) in the sample position and 0's everywhere else.

Figure 5A:
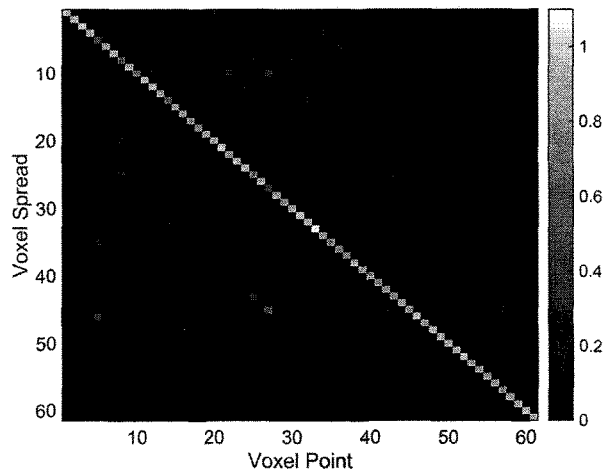
FIG. 5A represents the signals of the second proof of concept system corresponding to those of FIG. 5 for the first proof of concept system.

In FIG. 5 the primary frequency and harmonics measured from drive coil 1 are used to reconstruct between 1 and 12 voxel images. For coil 1, the primary frequency along with harmonics 2-6 were used in the reconstructions. Testing was performed by zigzagging across the voxel grid and so voxel 1 is closest to coil 1 and farthest from coil 2. The $R^2$ values are shown above each image. In conventional linear SMI, only a single voxel can be imaged so any position resolution above this threshold is evidence of increased spatial information from the nonlinear mNP response. FIG. 5A represents the signals of the second proof of concept system corresponding to those of FIG. 5 for the first proof of concept system.

In FIG. 5, the primary frequency and all of the harmonics measured from drive coil 2 were also used to reconstruct between 1 and 12 voxel images. For coil 2, the primary frequency along with harmonics 2-5 were used in the reconstructions. The results are similar and not presented here.

In FIG. 6, the primary frequencies of drive coils 1 and 2 as well as intermodulation frequencies measured from drive coils 1 and 2 were used to reconstruct between 1-12 voxel images. The observed intermodulation frequencies were $f_1+f_2$, $f_1+2f_2$, $f_1+3f_2$, $f_2+2f_1$ and $f_2+3f_1$.

During the testing illustrated in FIGS. 5 and 6, we observed that if the in-phase or out-of-phase data were used for image reconstruction only, the $R^2$ values would degrade rapidly. However, when the in-phase and out-of-phase data were used together, the $R^2$ values remained high for more voxels than expected. This is illustrated in FIG. 7 for the image reconstructions of primary frequencies and intermodulation frequencies. As illustrated, the $R^2$ values fall rapidly after 6 voxels for in-phase and out-of-phase image reconstructions when carried out separately but remain high for all 12 voxels when both measurement sets are used together.

Figure 8:
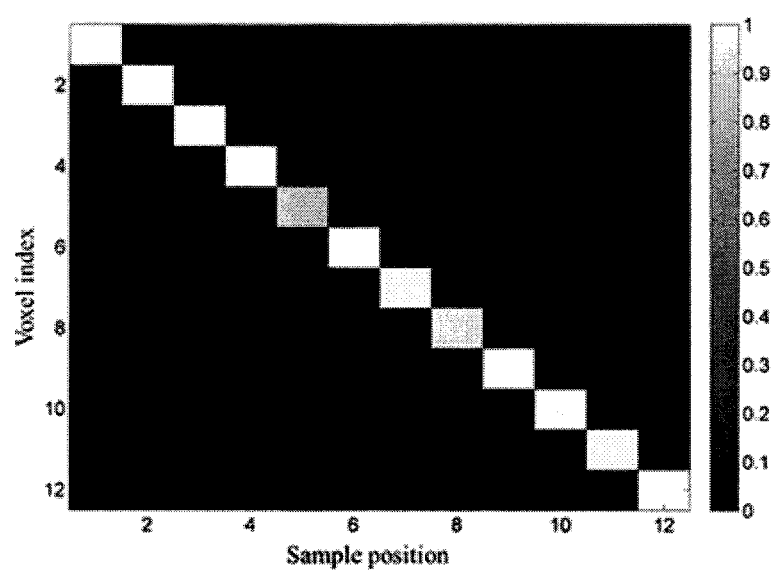
FIG. 8 illustrates results obtained by using both intermodulation and harmonic frequency data to reconstruct voxel locations.

To demonstrate the combined effects of primary frequencies, harmonic frequencies and intermodulation frequencies on SMI reconstruction, all data was combined in FIG. 8 to produce a 12 voxel nSMI. In this case $R^2$ was 0.996.

Figure 9:
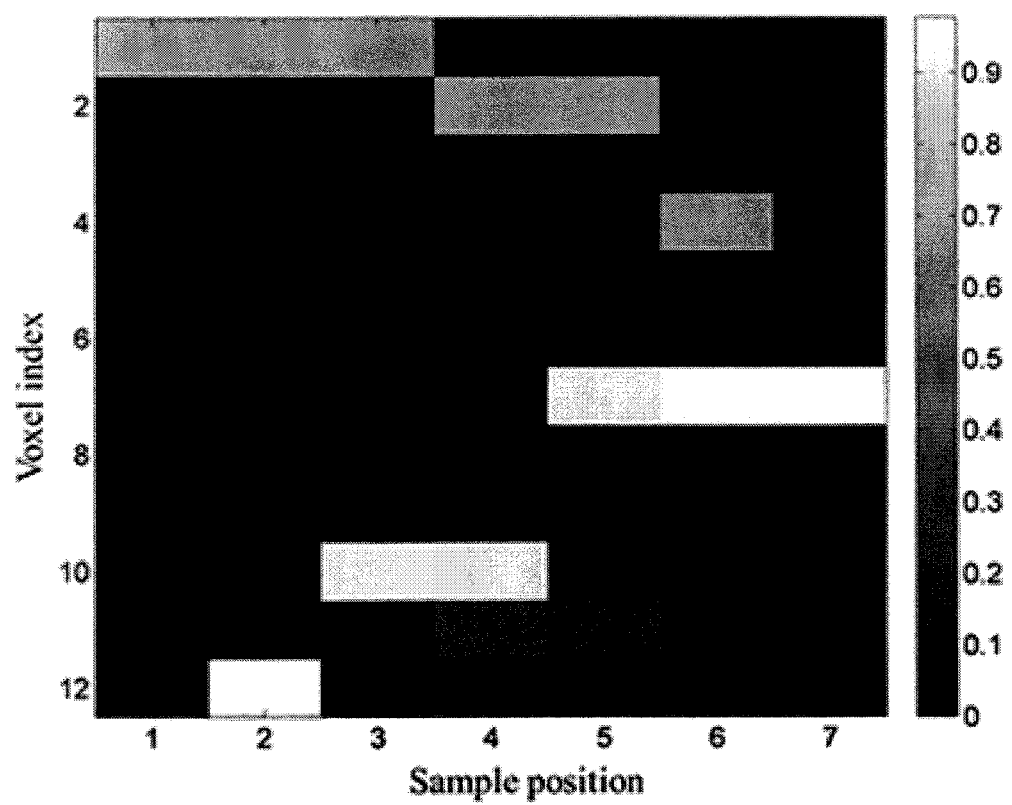
FIG. 9 illustrates results obtained with two nanoparticle concentrations in the imaging grid, using both intermodulation and harmonic frequency data to reconstruct voxel locations.

In real medical imaging, nanoparticles are expected to be present at more than one voxel location, and it is necessary to distinguish and map these. In order to evaluate distinguishing multiple nanoparticle concentrations, nSMI was conducted with two samples placed simultaneously in the imaging grid (FIG. 9) to illustrate that multiple concentrations can be located and distinguished with this method. In this case one of the samples was full concentration mNP solution and the other was a half concentration mNP solution. Due to the size of the Eppendorf tubes relative to the grid, it was not possible to place the samples adjacent to one another.

Figure 10:
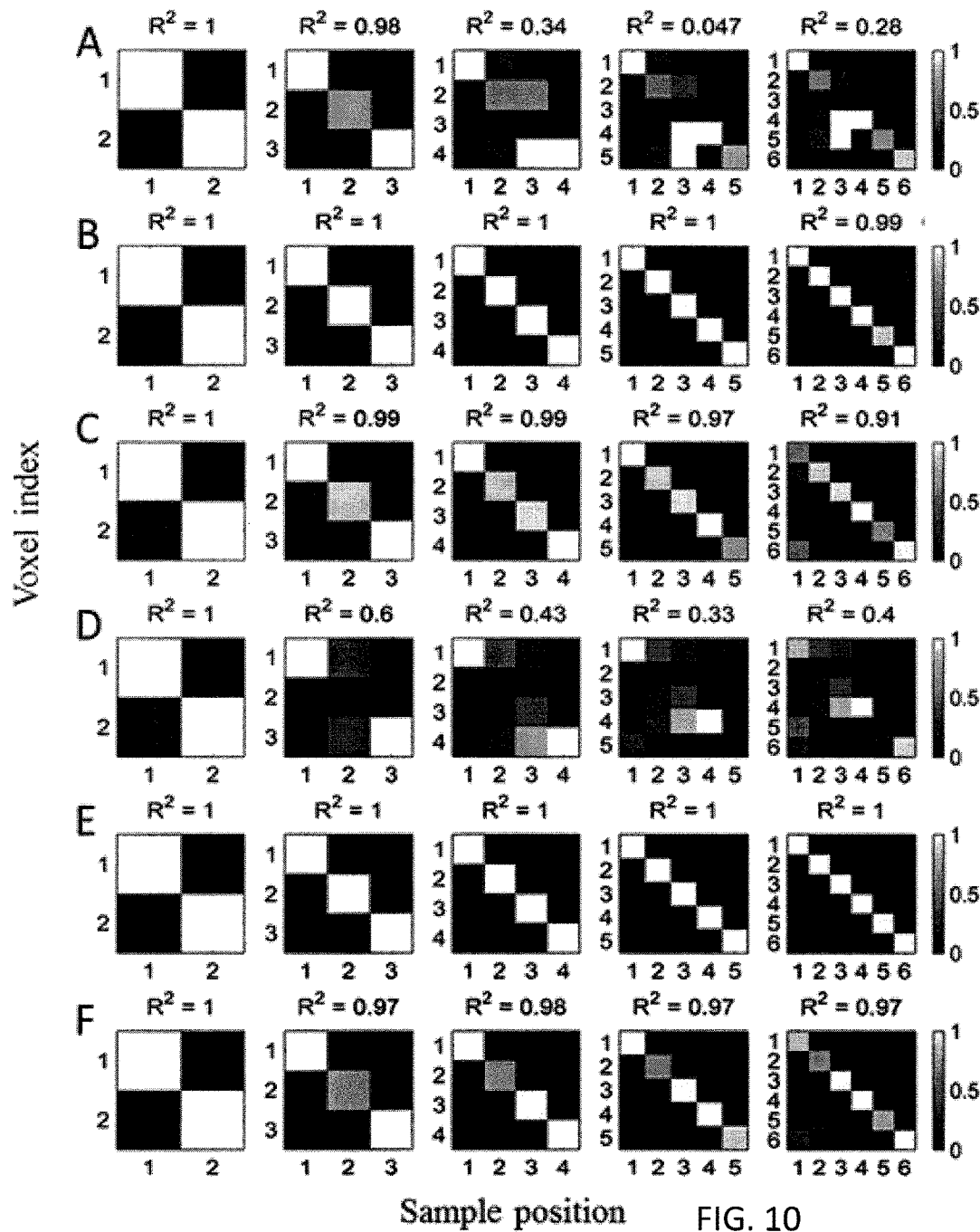
FIG. 10 illustrates results obtained using amplitude information, phase information, intermodulation information, or frequency information to reconstruct voxel concentrations.

Results obtained with the five additional time-multiplexed methods are shown in FIG. 10. As illustrated, between 2 and 6 voxels were reconstructed using only the $3^{rd}$ harmonic or the first intermodulation frequency of the data. $R^2$ values are shown for each of the six tests performed. Of these methods, four of the five showed an improvement in $R^2$ values compared with the control test. The asynchronous phase shifting methods showed the highest $R^2$ values of all the imaging methods tested, the frequency shifting method showed moderately high $R^2$ values. Amplitude modulation remained above $R^2=0.97$ except for 6 voxel reconstruction where it fell to $R^2=0.91$. The synchronous phase shifting method performed no better than the control test over the imaging conditions. In FIG. 10, A) Control condition with no parameter variation over the four test conditions.

B) Asynchronous phase shifting of one of the right drive coil.

C) Amplitude modulation of the drive current in one or both coils.

D) Synchronous phase shift for both coils.

E) Intermodulation asynchronous phase shifting.

F) Frequency shifting.

Figure 11:
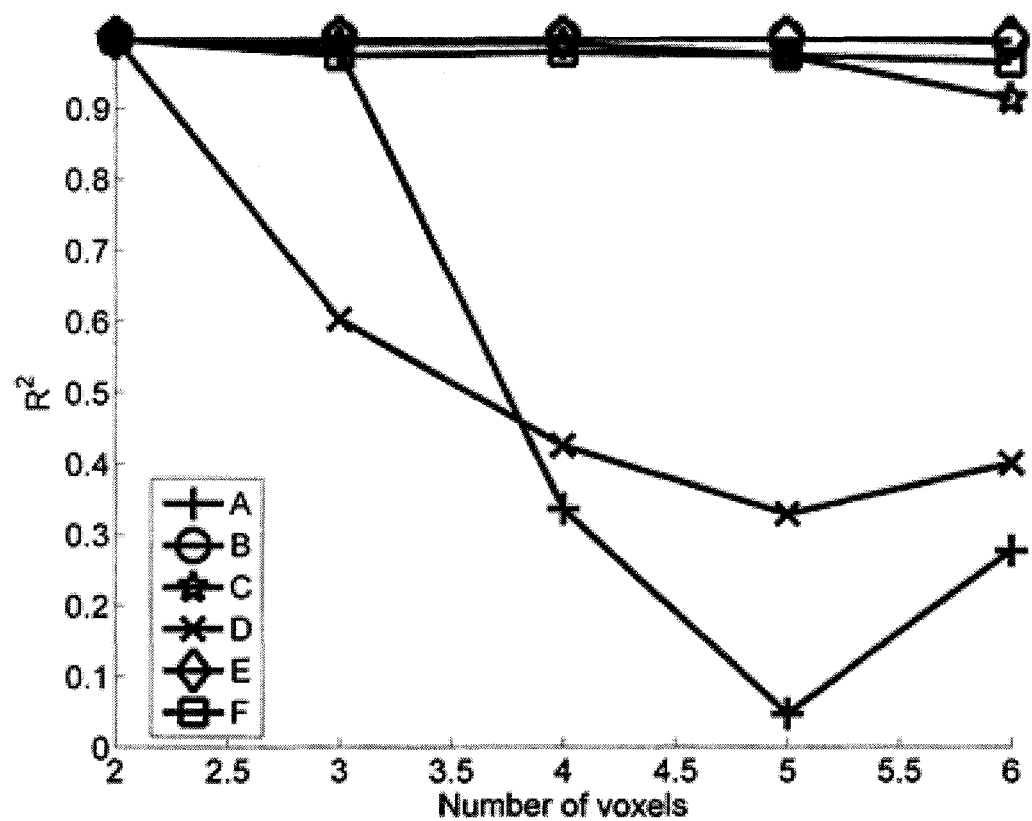
FIG. 11 illustrates $R^2$, or effectiveness, for the methods illustrated in FIG. 10.

A plot of the $R^2$ values for the control test and each of the five time-multiplexed methods is shown in FIG. 11. Four of the five methods remain above $R^2=0.9$ for up to six voxel reconstruction while the synchronous phase shifting method has a poor $R^2$ value after two voxel reconstruction.

Additional Resulting Images from the Second Proof of Concept System.

Figure 12:
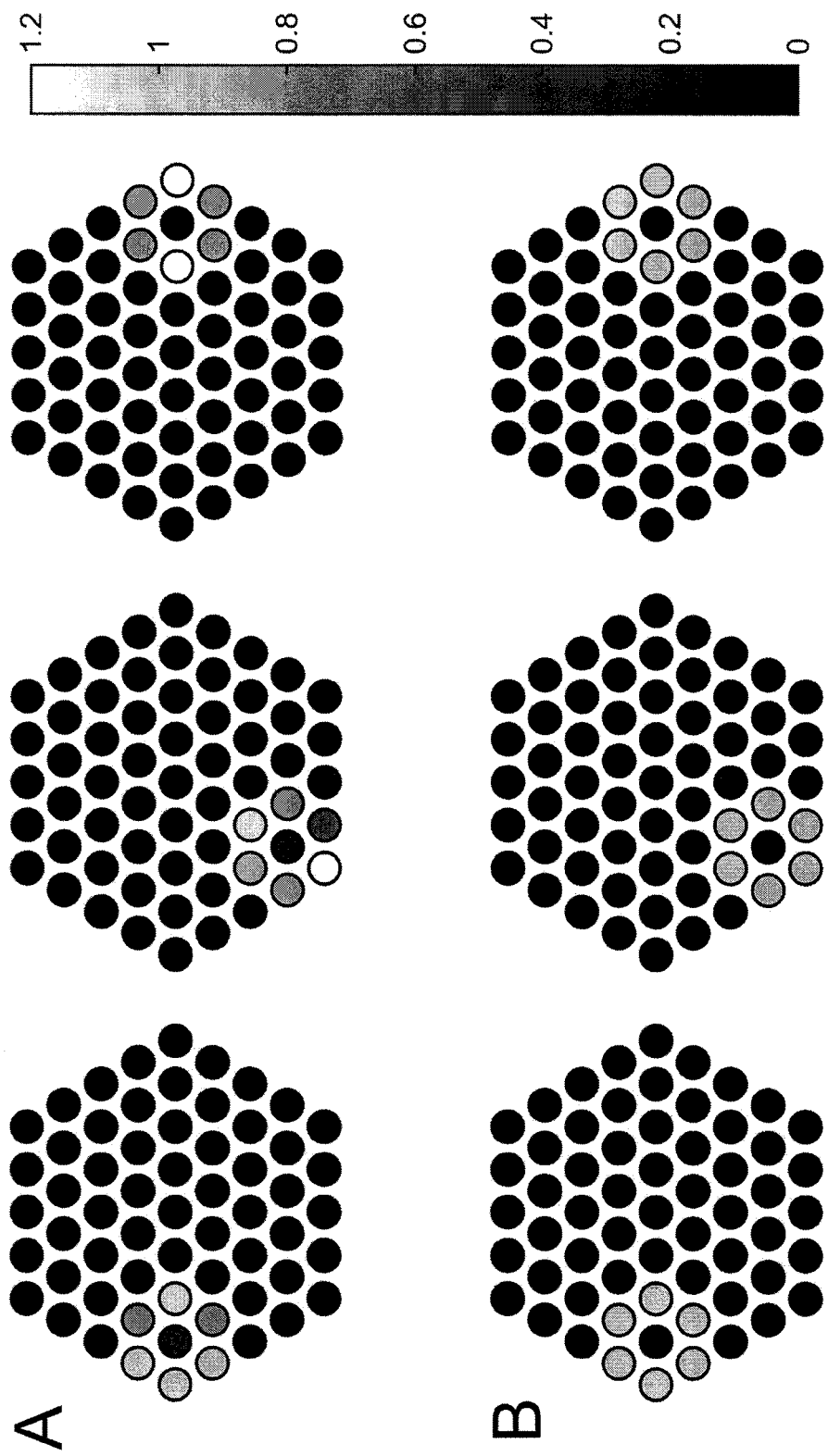
FIG. 12 illustrates hexagonal patterns of voxels containing magnetic nanoparticles imaged at various positions in the imaging grid of the second proof of concept system.

In FIG. 12, three hexagonal patterns are shown in various orientations on the imaging grid. The hexagonal patterns were readily distinguished. These three had the highest R2 values of the set of six at 0.94, 0.90 and 0.92 respectively. The remaining three hexagonal pattern SMIs are not shown but the $R^2$ values were 0.85, 0.80, and 0.78.

Figure 13:
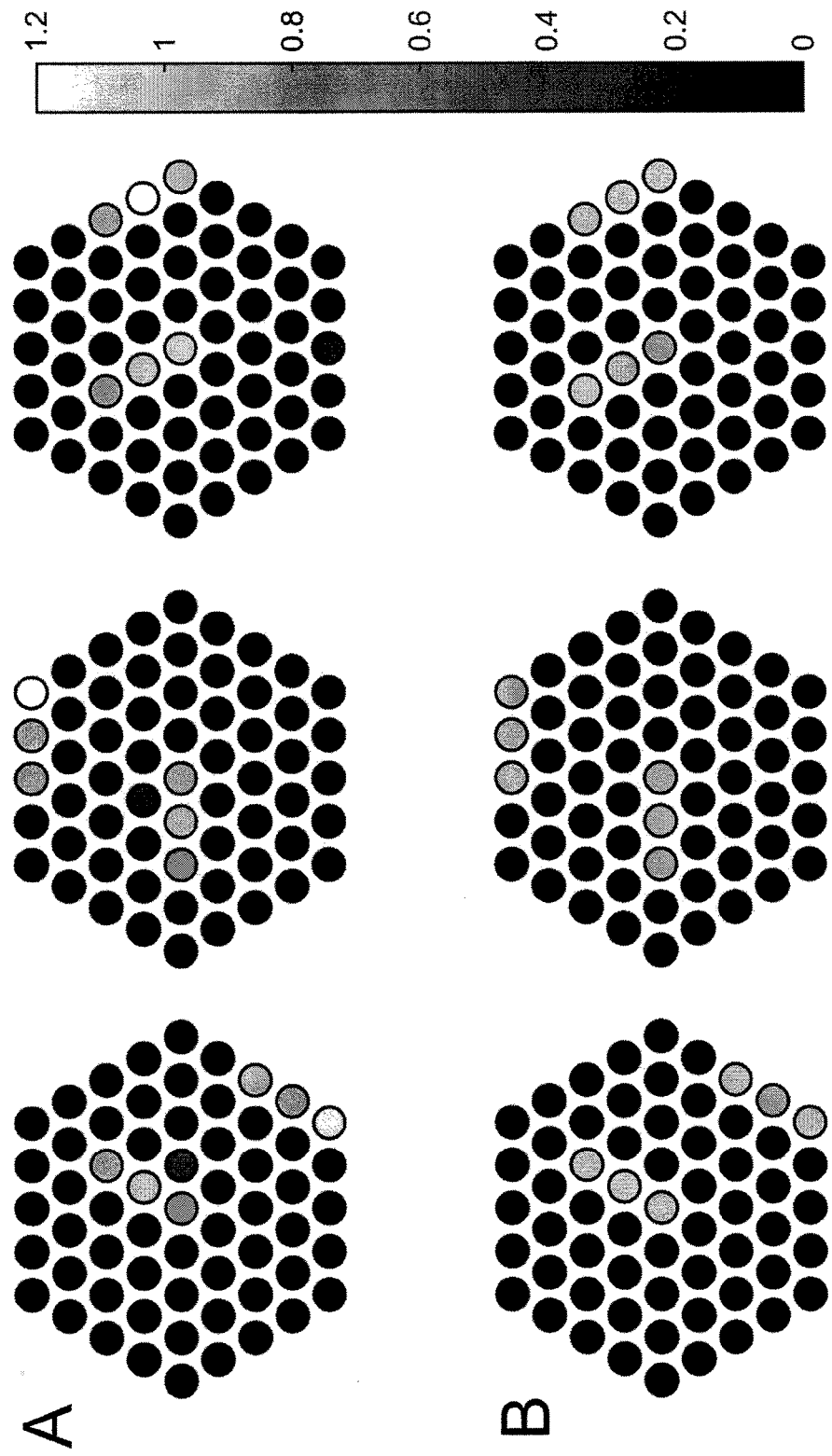
FIG. 13 illustrates bar patterns of voxels containing magnetic nanoparticles imaged at various positions in the imaging grid of the second proof of concept system.

In FIG. 13, three bar patterns are shown in various orientations in the imaging grid. These three bar patterns that had the best $R^2$ values at 0.96, 0.96 and 0.97 respectively. The remaining three SMIs of the bar patterns are not shown but had $R^2$ values of 0.95, 0.94 and 0.66.

Discussion and Conclusion

In this study we demonstrated a method of using the nonlinear magnetization response of mNPs to gain additional spatial information for SMI. We demonstrated how to use the magnetization of mNPs at harmonic frequencies from a single input coil to gain additional spatial information and demonstrated how intermodulation frequencies, resulting from two different applied magnetic fields at different AC frequencies, can also be used to gain additional spatial information. We then combined these effects to demonstrate how they can be used together to further improve SMI resolution. Drawing on an observation during this experimentation on the benefits of combining in-phase and out-of-phase data, we explored five time-multiplexed methods to give additional spatial information beyond the straightforward use of nonlinear mNP magnetization harmonics. Four of the five methods yielded an $R^2$ value higher than a control experiment. These were the asynchronous phase shifting methods, as well as the frequency and amplitude modulation methods corresponding to methods B, C, E and F from FIG. 4. These methods could potentially be used as a compounding factor to yield even more spatial information for nSMI.

Previously, we able to use three drive coils and two fluxgate sensors to reconstruct 6 imaging voxels. This level of resolution was achieved by combining data from three applied magnetic fields interacting with two sensors to give 6-voxel imaging. In the present study, we used two coils and one sensor and were able to reconstruct 12 voxels, which represents a six-fold improvement in voxels per sensor-coil pair over our prior work. This resolution improvement was also accomplished with a limited amount of harmonic and intermodulation data. In our reconstructions we were able to see a strong response from the first 4 harmonic frequencies, a limited response from $5^{th}$ and $6^{th}$ harmonics, and a strong response at 5 intermodulation frequencies. With an increased applied magnetic field strength we expect to see an improvement of up to a factor of 100 over our original version of SMI.

With the second proof of concept system, with 3 drive and 3 sensing coils oriented on perpendicular axes, and using the spatial information contained in harmonic frequencies and the different spatial patterns created with phase modulation, it was possible to reconstruct mNP images of hexagonal and bar patterns. In addition, we showed that a hexagonal pattern of saline was not recoverable, meaning that the SMI contrast was selective to the mNP samples.

In this second system, the images had 5-mm voxel spacing. However, the sample size was only 40 µL, which could fit into voxels of dimensions of 3.5 mm×3.5 mm×4.2 mm. The larger grid spacing used in the present study helped to distinguish adjacent voxels but we believe that given the high signal levels that we receive from each of the 61 locations, it will be possible to shrink the dimensions of the voxels in the future. In order to accurately image with higher spatial density it will be necessary to improve the quality of the samples and to use additional phase rotations for encoding. Both of these improvements are feasible and should help boost the number of voxels in an image to exceed 100 and reduce the voxel spacing to less than 5 mm. It is also feasible to extend the imaging grid into three dimensions for verification of the imaging system; and to substitute in-vivo tissue containing magnetic nanoparticles for the grid.

As was shown above, the mNPs characteristic phase response gives rise to different spatial information contained in the in-phase amplitudes and the out-of-phase amplitudes. This means that the in-phase and out-of-phase data contribute complementary information to the spatial reconstruction. In addition to exploring the use of the nonlinear magnetization for SMI, we also explored time-multiplexed methods to improve upon the results obtained in nSMI. These methods included, phase, frequency and amplitude modulation of one or both drive coils. These tests were performed in a time-multiplexed manner and it therefore took longer to acquire all of the imaging data. Asynchronous phase modulation methods yielded $R^2$ values of 1.00 for up to six voxels while the control could only reconstruct up to three voxels. Both the frequency and amplitude modulation were also able to reconstruct up to six voxels up with slightly lower $R^2$ values. This reduction in our experiment was primarily due to the inadequate strength of the applied magnetic fields, which were not strong enough to induce clear harmonics from all voxels. However, these methods show that it is possible to get even more spatial information by varying the amplitude, phase and frequency of the drive coils if longer data acquisition times can be tolerated.

The coil and sensor configuration used in the present study is most likely not optimal for nSMI. Several improvements could be made beyond increasing the applied magnetic field strength. Larger diameter coils could be used to increase imaging depth and an array of sensing coils and drive coils could be used, as illustrated in FIG. 2, to increase the imaging resolution beyond the added benefits of nonlinear effects. In addition, MPI uses frequencies in the kilohertz range, which reduces noise in the sensing coils, so adopting the use of frequencies in this range may help improve the signal to noise ratio.

The nSMI method may improve MPI resolution of a different nanoparticle imaging method called Magnetic Particle Imaging (MPI). Currently, the MPI method generally uses a field free point (FFP) to localize mNPs. An FFP is difficult to create because strong gradient fields are needed to generate a small FFP for high-resolution imaging. nSMI could be incorporated into MPI to eliminate the need for a FFP or to use the spatial information of harmonics within a broader, or even pseudoplanar, FFP to improve resolution. In a 3 dimensional FFP, doubling the resolution would require 8 voxels, less than the number demonstrated in this study. This would however involve some tradeoff in mNP sensitivity due to imaging reducing the amount of harmonic averaging.

The present study provides a clear path for the development of a high resolution SMI system that could have applications in medicine. It is anticipated that such a system could have multiple AC driving coils, where the driving coils are configured to provide AC magnetic field gradients into the imaging zone, and where the driving coils are each time multiplexed between two or more driving frequencies, phases, and amplitudes during imaging. Further, such a system may have DC or static field magnets or coils configured to provide a bias field and a DC gradient to the imaging zone, and that the DC gradient may be switched or rotated during imaging. The system will also have magnetic field sensors configured to sense fields from the imaging zone, and signal processing electronics configured to measure harmonics and intermodulation products of the driving frequencies. The system will also have an image processor configured to construct a voxel-based image of magnetic nanoparticle concentrations in the imaging zone based upon the measured harmonics and intermodulation products, thereby taking advantage of nonlinear responses of the magnetic nanoparticles to determine positions of the nanoparticles in the imaging zone.

To realize SMI as a useful medical imaging technology, we believe that we can ultimately scale up the system until 1-mm resolution is achieved in three dimensions. In the present work, we added additional excitation and detection coils and we believe that further expansion is possible. In order to reduce the imaging resolution to the 1-mm scale, it will be necessary to increase the magnetic field strength beyond the few millitesla level used in the present study and to use excitation coils that are capable of delivering tens of millitesla at several centimeters of depth. This increase in field strength will add some additional size and complexity to our current system but could ultimately prove invaluable for high density imaging as the higher magnetic field gradients will provide many more harmonics and intermodulation frequencies.

Applicant notes that most embodiments of the imaging system herein described do not apply a DC magnetic field strong enough to magnetically saturate the magnetic nanoparticles anywhere in the imaging zone. Most embodiments may therefore be distinguished by the relatively low magnetic fields in all parts of the imaging zone, such as 30 millitesla or less.

Upgrading MPI, and Differences from Standard MPI

Figure 14:
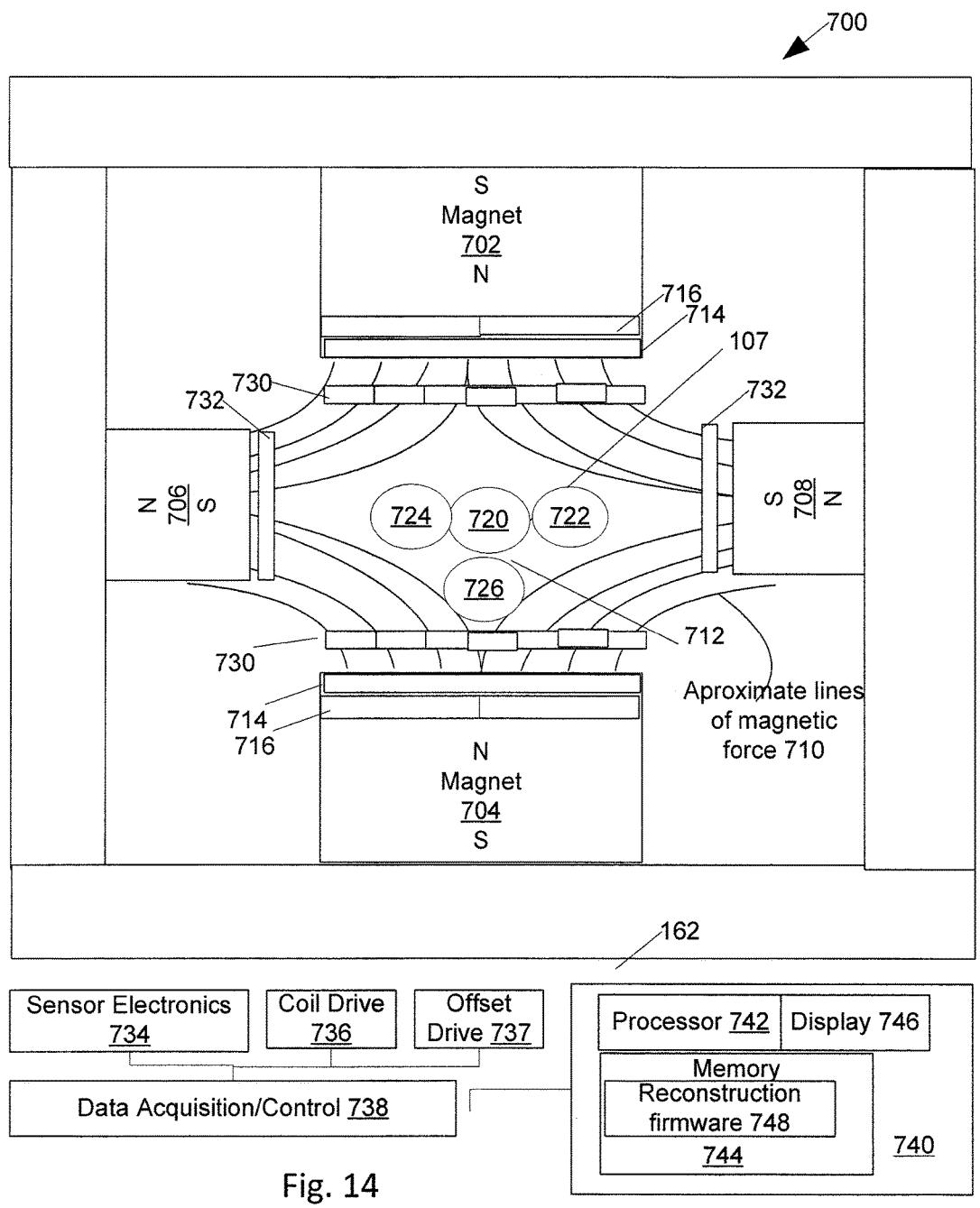
FIG. 14 illustrates a combination of our harmonic, frequency, and phase-encoded magnetic nanoparticle position determination system into an MPI system.

The characteristic features of magnetic particle imaging (MPI), the most salient prior magnetic nanoparticle imaging technique, is that in MPI, strong DC or slowly changing gradients are used to encode position—usually by dividing the imaging zone into a relatively small unsaturated zone and larger fully-saturated zone or zones—and the AC field is used to probe the quantity of magnetic particles in the unsaturated zone using magnetic sensors. This unsaturated zone can be a point (a field free point FFP), a field-free line (FFL), a field-free surface, or other geometry. An embodiment of an MPI machine 700 upgraded with phase and intermodulation product resolution enhancement is illustrated in FIG. 14. Such a machine has main magnets 702, 704 with like poles, such as magnetic north poles, facing each other such that the magnets are repelled from each other and a region of lower field strength containing an imaging zone 712 arises between the magnets, as illustrated by approximate magnetic lines of force 710. Within the imaging zone is a field free zone 720, that is actually an unsaturated zone, surrounded by, typically larger, saturated zones. Additional pole pieces 706, 708 or magnets may also be used to control the magnetic field. At each magnet 702, 704, there are additional electromagnets, such as vertical coils 714 and gradient coils 716 configured such that when they are appropriately energized the field free or unsaturated zone 720 can be shifted in multiple axes to alternative field free zone positions 722, 724, 726, as known in the art of MPI. The enhanced machine, however, has at least one driving coil array 730 of many driving coils located at the pole pieces, or between pole pieces and the imaging zone, instead of traditional single, large, driving coils. The machine also has sensing coils 732 coupled to sensor electronics 734 and coil drivers 736 coupled to the drive coil array 730, both sensor electronics and coil drivers controlled by data acquisition and control system 738. The gradient and vertical coils 714, 716 are coupled to be driven by offset drivers 737 also controlled by data acquisition and control system 738. Data acquisition and control system 738 operates under control of, and provides data to, an image processing system 740 having a processor 742, memory 744 and image display subsystem 746, with image reconstruction firmware 748 in memory 744.

In operation, enhanced system 700 operates by first using the offset coil drivers to position the field free or unsaturated zone 720 at a desired imaging position in the imaging zone, then using the driving coil drivers to apply AC driving signals simultaneously to three or more driven coils of the drive coil array that are spatially near the imaging position. The driven coils are each driven with two or more frequencies of AC signals such that nonlinear responses of magnetic nanoparticles in the imaging position will produce both harmonics and intermodulation products. Further, phase encoding is provided to the imaging zone by driving the driven coils with phase-shifted signals in at least a first pattern of phases and a second pattern of phases. Signals from the imaging position are detected by the sense coils 732 and processed as herein described to provide a 3-dimensional map of nanoparticle locations within the unsaturated imaging position. In an alternative embodiment, the phase encoding is supplemented with adjustable amplitude encoding and a unique frequency for each coil to permit location through intermodulation products Once a 2 or preferably a 3-dimensional, voxel-based, map of nanoparticle locations within the currently selected field free or unsaturated imaging position is created, these are saved in associated voxels of an overall voxel-based map of the imaging zone and the image processing system 740 signals the offset drivers 737 to shift the imaging position to other, alternative, imaging positions 722, 724, 276 within the imaging zone 712 such that nanoparticle concentrations at additional voxels of the overall voxel-based map of nanoparticle positions can be determined.

The system 700 differs from standard MPI in that the inverse Radon transform need not be used, and in that the AC fields applied in embodiments of the present system have phase gradients, and in some embodiments frequency gradients, to permit phase and intermodulation product encoding of nanoparticle position.

Outline of Operation

The characteristic features of traditional magnetic particle imaging (MPI), the most salient prior magnetic nanoparticle imaging technique, is that in MPI, strong DC gradients are used to encode position—usually by dividing the imaging zone into a relatively small unsaturated zone and larger fully-saturated zone or zones—and the AC field is used to probe the quantity of magnetic particles in the unsaturated zone using magnetic sensors. While the magnitude of DC field required to saturate the magnetic particles varies somewhat with the particle type, for Resovist nanoparticles signals can be achieved at field strengths up to about 30 millitesla, but above 100 millitesla the particles saturate and signal vanishes; for purposes of this document any zone with DC field above 100 millitesla is assumed to be a saturated zone. This unsaturated zone can be a point (a field free point FFP), a field-free line (FFL), a field-free surface, or other geometry. Such an AC applied field elicits responses from the magnetic particles in the unsaturated zone including harmonics, and these responses scale linearly with the quantity of the particles in the unsaturated zone. The ideal AC field for traditional MPI does not have a gradient and the ideal DC field for MPI has large magnitude gradients so that the unsaturated zone is sharply defined resulting in high resolution imaging. Encoding of position with MPI requires changing the DC fields to alter the location, shape and/or orientation of the unsaturated zone in an overall imaging zone. Position is decoded in MPI from the location of the unsaturated zone.

A fundamental difference in our method vs MPI is our primary position encoding using the nonlinear frequency responses of the magnetic particles:

In our system there is also a magnetically unsaturated zone, which is typically the entire imaging zone but could, in some embodiments, be restricted to a subset of the imaging zone by DC gradients as in MPI. Our system applies an AC magnetic field that typically has gradients in amplitude, phase and/or frequency, and elicits nonlinear responses from the magnetic particles including harmonics and phases, and, in multi-frequency embodiments, intermodulation products, and recovers position directly from those nonlinear responses. We also may in some embodiments apply a DC field to the imaging zone to alter those harmonics and intermodulation products to get additional imaging information. Our method requires that there be a gradient within the unsaturated zone from either the AC field, DC field, or both fields in combination to provide for our spatial encoding. Our imaging routine extracts position information from the magnetic particles in the unsaturated zone from the relative amplitudes and phases of the harmonics and intermodulation products that are sensed. We could call this position encoding from the nonlinear frequency response of the magnetic particles. In our system, nanoparticle position is decoded from the nonlinear frequency response using prior knowledge of the response characteristics of the magnetic particles and the AC and DC gradients over an unsaturated zone.

Now for a second aspect of position encoding in our method—position encoding by AC field modulation:

Position encoding with our method is not limited to dimensions or locations of a fixed or movable unsaturated zone or fixed gradients within that zone. We obtain a second level of position encoding information by varying the levels and gradients in the AC fields. The gradients from the AC field over the unsaturated zone generated by using different, phase, amplitude, and/or frequency on each driven coil of our driving coil array, and then changing those phases, amplitudes, and/or frequencies to obtain different AC field gradients and yield yet more position-encoded data. Under ideal operating conditions, the position encoding information from AC field modulations provides a multiplicative gain in the position encoding information when combined with the nonlinear frequency response encoding. The variations in AC field levels and gradients are also captured in our imaging model.

There is another aspect of position encoding in some embodiments of our method—position encoding by DC field modulation:

Our method also encodes information by varying the DC field gradient over the unsaturated zone without substantially moving the unsaturated zone while doing so. Whereas a pure AC field and gradient over the unsaturated zone will result in even harmonics of various phases and intermodulation products for position encoding, a DC field biases the nonlinear AC responses of the magnetic particles towards odd harmonics and intermodulation products yielding additional position encoding information. By varying the DC field level and varying the DC field gradient over the unsaturated zone, the net AC and DC fields applied to the magnetic particles will be altered in the unsaturated zone thereby encoding information. Under ideal conditions, the position information gained from DC field modulation will be additive with the AC field modulation and multiplicative with the nonlinear frequency response encoding. The variations in DC field gradients are also captured in our imaging model.

Another aspect of position encoding in our method may also include varying the geometry of the unsaturated zone:

While many of our embodiments lack a saturated zone, we can use our method in a system having a saturated zone by combining the position encoding methods of MPI (where unsaturated zone geometry and position is varied to encode position) with our phase and intermodulation product encoding to further encode position of the magnetic particles. In this variation of our method, DC field levels are increased sufficiently to saturate different regions of the imaging zone leaving an unsaturated zone; we then apply our AC field gradients and image within the unsaturated zone using phase, harmonic, and intermodulation encoding of position. This allows use of our method with MPI to enhance resolution of MPI, allow for similar resolution to be achieved with weaker DC field gradients and therefore lower-cost hardware than traditional MPI systems, or to decrease imaging time.

Combinations

The imaging system herein described may be built with various combinations of the components herein described. Among those combinations are as follows A magnetic particle imaging system adapted for imaging magnetic nanoparticles or magnetic microparticles and designated A has at least a first driving coil, the first driving coil coupled to a first AC driving circuit operable at a first frequency and configured to provide magnetic fields and field gradients to an imaging zone; at least one magnetic sensor positioned to sense magnetic fields from the imaging zone; and signal processing apparatus for determining at least magnitude and phase of at least a first harmonic frequencies of the driving coil. In this system, the signal processing apparatus is further configured to map the location of nanoparticles in the imaging zone based upon at least the magnitudes and phases of the harmonics of the first frequency.

A magnetic particle imaging system designated AAA incorporating the system designated A and wherein the magnetic fields within the imaging zone are insufficiently strong to maintain magnetic particles in magnetic saturation for a period in excess of a cycle of the first AC driving circuit.

A system designated AA incorporating the system designated A or AAA wherein at least one static magnet is positioned to provide a static magnetic field to the imaging zone, the static magnetic field having a gradient within the imaging zone.

A system designated AB incorporating the system designated A, AAA, or AA wherein the first AC driving circuit is configured to time multiplex between the first frequency and a second frequency.

A system designated AC incorporating the system designated A, AAA, AA, or AB wherein the first AC driving circuit is configured to time multiplex an amplitude of the first driving coil between a first and a second amplitude.

A system designated AD incorporating the system designated A, AAA, AA, AB, or AC, further including a second driving coil coupled to be driven by a second AC driving circuit and, wherein the first and second AC driving circuits operate at different frequencies.

A system designated ADA incorporating the system designated A, AA, AAA, AB, or AC, further including a second driving coil coupled to be driven by a second AC driving circuit, wherein each driving coil is operated at two frequencies simultaneously.

A system designated AE incorporating the system designated A, AA, AAA, AB, AC, or AD further including a second driving coil coupled to be driven by a second AC driving circuit and oriented on an axis parallel to the axis of the first driving coil, wherein the first and second AC driving circuits operate at the same frequency but with a predeterminable phase offset between the first and second driving coils.

A system designated AF incorporating the system designated A, AA, AAA, AB, AC, AD, or AE further including a second magnetic sensor positioned to sense field on an axis perpendicular to the driving coils.

A system designated AFA incorporating the system designated A, AA, AAA, AB, AC, AD, or AE further including a second magnetic sensor positioned to sense field on an axis that is not perpendicular to the driving coils.

A magnetic nanoparticle imaging system designated B having: a first driving coil coupled to a first AC driving circuit operable at a first frequency, and a second driving coil coupled to a second AC driving circuit operable at a second frequency, the first and second frequencies being different, the first and second driving coils positioned to provide magnetic fields and field gradients to an imaging zone. The system has at least one magnetic sensor positioned to sense magnetic fields from the imaging zone; and signal processing apparatus for determining at least magnitude and phase at intermodulation products of signals at the first and second frequencies; wherein the signal processing apparatus is also capable of determining at least signal magnitude and phase of at least a first and a second harmonic of the first frequency; and wherein the signal processing apparatus is further configured to map location of nanoparticles in the imaging zone based upon at least the magnitudes and phases of harmonics of the first frequency and the magnitude of the intermodulation products.

A magnetic nanoparticle imaging system designated BA including the system designated B wherein a static bias field magnet positioned to provide a static magnetic field and/or gradient magnetic field to the imaging zone.

A magnetic nanoparticle imaging system designated BA including the system designated B wherein the first AC driving circuit is configured to time multiplex frequency of the first driving coil between the first frequency and a third frequency.

A magnetic nanoparticle imaging system designated BB including the system designated B or BA wherein the first AC driving circuit is configured to time multiplex an amplitude of the first driving coil between a first and a second amplitude A magnetic nanoparticle imaging system designated BC including the system of designated B, BA, or BB wherein the first AC driving circuit is configured to time multiplex a phase of the first driving coil between a first and a second phase A magnetic nanoparticle imaging system designated BC including the system designated B, BA, BB, or BC further comprising a third driving coil coupled to a third AC driving circuit configured to operate at a third frequency, the first, second, and third frequencies being different.

A magnetic nanoparticle imaging system designated BD including the system designated B, BA, BB, or BC, further including a static magnet configured to provide a DC bias field to the imaging zone.

A magnetic nanoparticle imaging system designated BDA including the system designated BD wherein the DC bias field has a DC gradient in the imaging zone.

A magnetic nanoparticle imaging system designated BDB including the system designated BDA further comprising apparatus to alter the DC gradient in the imaging zone.

A magnetic particle imaging system designated C and adapted for imaging nanoparticles of average diameter between 5 and 250 nanometers, or for imaging microparticles of average size between 250 and 2500 nanometers, including: at least a first and a second driving coil, the first driving coil coupled to a first AC driving circuit operable at a first frequency, the second driving coil coupled to a second AC driving circuit operable at the first frequency, the driving coils configured to provide magnetic fields and field gradients to an imaging zone; at least one magnetic sensor positioned to sense magnetic fields from the imaging zone; and signal processing apparatus for determining at least magnitude and phase of at least one harmonic frequency of the driving coil; and wherein the signal processing apparatus is further configured to map the location of magnetic nanoparticles in the imaging zone based upon at least the magnitudes and phases of the at least one harmonic of the first frequency. In this system, the first and second AC driving circuits are adapted to provide a first and a second predetermined phase shift between drive to the first driving coil at the first frequency and drive to the second driving coil at the first frequency, the first and second predetermined phase shifts being unequal.

A system designated CA including the system designated C wherein at least one static magnet is positioned to provide a static magnetic field to the imaging zone, the static magnetic field having a gradient within the imaging zone and the static magnetic field insufficiently strong to maintain the magnetic particles in magnetic saturation anywhere in the imaging zone.

A system designated CB including the system designated C or CA, wherein the first AC driving circuit is configured to drive the first driving coil at a first and a second frequency simultaneously, and wherein the signal processing apparatus is configured to map the location of magnetic nanoparticles based upon at least one intermodulation product of the first and second frequency.

A system designated CC including the system designated CB wherein the second driving circuit is configured to drive the second coil at the first frequency and a third frequency simultaneously.

A system designated CD including the system designated CC wherein the second and third frequency are equal, and wherein the first and second AC driving circuits are adapted to provide a first and a second predetermined phase shift between drive to the first driving coil at the second frequency and drive to the second driving coil at the third frequency, the first and second predetermined phase shifts being unequal.

A system designated CE including the system designated CC wherein the second and third frequency differ.

A system designated CF including the system designated CC or CD, wherein the first AC driving circuit is adapted to drive a DC current into the first driving coil, the DC current superimposed on AC current of the first driving coil and thereby cause the first driving coil to provide a DC magnetic field superimposed on an AC magnetic field.

A system designated CG including the system designated CC, DD, or CE further comprising electromagnets adapted to provide a saturated zone and a moveable unsaturated zone within the imaging zone, and wherein the signal processing apparatus is configured to position the unsaturated zone at a first location in the imaging zone, map first nanoparticle locations, relocate the unsaturated zone to a second location in the imaging zone, map second nanoparticle locations, and to produce a composite nanoparticle location map from both the first and second nanoparticle location maps.

A magnetic particle imaging system designated D adapted for imaging nanoparticles of average diameter between 5 and 250 nanometers, or for imaging microparticles of average size between 250 and 2500 nanometers, including: at least a first driving coil, the first driving coil coupled to a first AC driving circuit operable at a first frequency and configured to provide magnetic fields and field gradients to an imaging zone; at least one magnetic sensor positioned to sense magnetic fields from the imaging zone; and signal processing apparatus for determining at least magnitude and phase of at least a first harmonic frequencies of the driving coil; and wherein the signal processing apparatus is further configured to map the location of nanoparticles in the imaging zone based upon at least the magnitudes and phases of the harmonics of the first frequency, wherein the magnetic fields within the imaging zone are insufficiently strong to maintain the magnetic particles in magnetic saturation for a period in excess of a cycle of the first AC driving circuit anywhere in the imaging zone.

A system designated DA including the system designated D wherein at least one static magnet is positioned to provide a static magnetic field to the imaging zone, the static magnetic field having a gradient within the imaging zone and the static magnetic field insufficiently strong to maintain the magnetic particles in magnetic saturation anywhere in the imaging zone.

A system designated DB including the system designated D wherein the first AC driving circuit is configured to time multiplex between the first frequency and a second frequency.

A system designated DC including the system designated D wherein the first AC driving circuit is configured to time multiplex an amplitude of the first driving coil between a first and a second amplitude.

A system designated DD including the system designated D, wherein the first AC driving circuit is configured to drive the first driving coil at a first and a second frequency simultaneously, and wherein the signal processing apparatus is configured to use intermodulation products between the first and second frequency in mapping nanoparticle locations.

A system designated DE including the system designated DD or D further comprising a second driving coil coupled to be driven by a second AC driving circuit, wherein the second driving coil is operated at a third and a fourth frequency simultaneously.

A system designated DF including the system designated DE wherein the first and third frequency are equal.

A system designated DG including the system designated DE, wherein the second and fourth frequency differ.

A system designated DH including the system designated DD, DE, DF, or DG wherein the signal processing apparatus is configured to change at least the first driving coil operating frequencies from a first frequency or phase to a fifth frequency, and to map nanoparticle concentration locations from data acquired while the driving coil is operated at both the first frequency and the fifth frequency.

A system designated DI including the system designated DD wherein the first AC driving circuit is adapted to drive a DC current into the first driving coil, the DC current superimposed on AC current of the first driving coil and thereby serve as the static magnet.

A system designated DH including the system designated DE wherein the first and second AC driving circuits operate at the same frequency but at either a first and a second distinct predetermined phase offset between the first and second driving coils and where the signal processing apparatus is configured to acquire phase data at the first and second phase offsets.

A system designated DI including the system designated D, DA, DB, DC, DD, DE, DF, DG, or DH wherein the at least one magnetic sensor comprises at least two magnetic sensors positioned to sense field on an axis perpendicular to the driving coils.

A system designated CDA including the system designated CD or DD wherein the first AC driving circuit is configured to time multiplex an amplitude of the first driving coil between a first and a second amplitude.

A magnetic nanoparticle imaging system designated E including: a first driving coil coupled to a first AC driving circuit operable at a first frequency, and a second driving coil coupled to a second AC driving circuit operable at a second frequency, the first and second frequencies being different, the first and second driving coils positioned to provide magnetic fields and field gradients to an imaging zone; at least one magnetic sensor positioned to sense magnetic fields from the imaging zone; and signal processing apparatus for determining at least magnitude and phase at intermodulation products of signals at the first and second frequencies; wherein the signal processing apparatus is also capable of determining at least signal magnitude and phase of at least a first and a second harmonic of the first frequency; and wherein the signal processing apparatus is further configured to map location of nanoparticles in the imaging zone based upon at least the magnitudes and phases of harmonics of the first frequency and the magnitudes and phases of the intermodulation products.

A system designated EA including the system designated E wherein a static bias field magnet is positioned to provide a static magnetic field and/or gradient magnetic field to the imaging zone.

A system designated EB including the system designated EA wherein the first AC driving circuit is configured to time multiplex frequency of the first driving coil between the first frequency and a third frequency.

A system designated ED including the system designated EA further including a third driving coil coupled to a third AC driving circuit configured to operate at a third frequency, the first, second, and third frequencies being different.

A method designated F of imaging magnetic nanoparticles in an imaging zone including: applying an AC driving magnetic field to the imaging zone at a first and a second frequency; applying a DC magnetic field gradient to the imaging zone, the DC magnetic field inadequate to saturate magnetic nanoparticles anywhere in the imaging zone, measuring magnetic fields from the imaging zone to provide data with at least two sensors; analyzing the data for phase, harmonics and intermodulation products of the first and second frequencies; and generating a map of locations and concentrations of the magnetic nanoparticles based upon the harmonics and intermodulation products of the first and second frequencies.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A magnetic particle imaging system adapted for imaging magnetic particles selected from the group consisting of magnetic nanoparticles of average diameter between 5 and 250 nanometers, and magnetic microparticles of average diameter between 250 and 2500 nanometers, comprising:
   at least first and second driving coils, the first driving coil coupled to a first AC driving circuit operable at a first frequency, the second driving coil coupled to a second AC driving circuit operable at the first frequency, the first and second driving coils configured to provide magnetic fields and field gradients to an imaging zone;
   at least one magnetic sensor positioned to sense magnetic fields from the imaging zone; and a signal processing apparatus for determining at least magnitude and phase of at least one harmonic frequency of the first and second driving coils; and wherein the signal processing apparatus is further configured to map a location of magnetic nanoparticles in the imaging zone based upon the at least magnitudes and phases of the at least one harmonic of the first frequency;

wherein the first and second AC driving circuits are adapted to provide first and second predetermined phase shifts between drive to the first driving coil at the first frequency and drive to the second driving coil at the first frequency, the first and second predetermined phase shifts being unequal.

2. The system of claim 1 wherein at least one static magnet is positioned to provide a static magnetic field to the imaging zone, the static magnetic field having a gradient within the imaging zone and the static magnetic field insufficiently strong to maintain the magnetic particles in magnetic saturation anywhere in the imaging zone.

3. The system of claim 1, wherein the first AC driving circuit is configured to drive the first driving coil at the first frequency and a second frequency simultaneously, and wherein the signal processing apparatus is configured to map the location of magnetic nanoparticles based upon at least one intermodulation product of the first and second frequency.

4. The system of claim 3, wherein the second driving circuit is configured to drive the second coil at the first frequency and a third frequency simultaneously.

5. The system of claim 4, wherein the second and third frequencies are equal, and wherein the first and second AC driving circuits are adapted to provide a first and a second predetermined phase shift between drive to the first driving coil at the second frequency and drive to the second driving coil at the third frequency, the first and second predetermined phase shifts being unequal.

6. The system of claim 4, wherein the second and third frequencies differ.

7. The system of claim 5, wherein the first AC driving circuit is adapted to drive a DC current into the first driving coil, the DC current superimposed on AC current of the first driving coil and thereby cause the first driving coil to provide a DC magnetic field superimposed on an AC magnetic field.

8. The system of claim 5, further comprising electromagnets adapted to provide a saturated zone and a moveable unsaturated zone within the imaging zone, and wherein the signal processing apparatus is configured to position the unsaturated zone at a first location in the imaging zone, map first nanoparticle locations, relocate the unsaturated zone to a second location in the imaging zone, map second nanoparticle locations, and to produce a composite nanoparticle location map from both the first and second nanoparticle location maps.

9. A magnetic particle imaging system adapted for imaging magnetic nanoparticles of average diameter between 5 and 250 nanometers, or for imaging magnetic microparticles of average diameter between 250 and 2500 nanometers, comprising:

at least a first driving coil, the first driving coil coupled to a first AC driving circuit operable at a first frequency and configured to provide magnetic fields and field gradients to an imaging zone;

at least one magnetic sensor positioned to sense magnetic fields from the imaging zone; and a signal processing apparatus for determining at least magnitude and phase of at least a first harmonic frequency of the first driving coil; and wherein the signal processing apparatus is further configured to map a location of the magnetic nanoparticles or microparticles in the imaging zone based upon the at least magnitudes and phases of the harmonics of the first frequency, wherein the magnetic fields within the imaging zone are insufficiently strong to maintain the magnetic nanoparticles or magnetic microparticles in magnetic saturation for a period in excess of a cycle of the first AC driving circuit anywhere in the imaging zone.

10. The system of claim 9 wherein at least one static magnet is positioned to provide a static magnetic field to the imaging zone, the static magnetic field having a gradient within the imaging zone and the static magnetic field insufficiently strong to maintain the magnetic nanoparticles or microparticles in magnetic saturation anywhere in the imaging zone.

11. The system of claim 10, wherein the first AC driving circuit is configured to time multiplex between the first frequency and a second frequency.

12. The system of claim 10, wherein the first AC driving circuit is configured to time multiplex an amplitude of the first driving coil between a first and a second amplitude.

13. The system of claim 10, wherein the first AC driving circuit is configured to drive the first driving coil at the first frequency and a second frequency simultaneously, and wherein the signal processing apparatus is configured to use intermodulation products between the first and second frequencies in mapping magnetic nanoparticle locations.

14. The system of claim 13 further comprising a second driving coil coupled to be driven by a second AC driving circuit, wherein the second driving coil is operated at a third and a fourth frequency simultaneously.

15. The system of claim 14, wherein the first and third frequencies are equal.

16. The system of claim 14, wherein the second and fourth frequencies differ.

17. The system of claim 10, wherein the signal processing apparatus is configured to change at least the first driving coil operating frequencies from the first frequency to a fifth frequency, and to map nanoparticle concentration locations from data acquired while the driving coil is operated at both the first frequency and the fifth frequency.

18. The system of claim 10, wherein the first AC driving circuit is adapted to drive a DC current into the first driving coil, the DC current superimposed on AC current of the first driving coil and thereby serve as a static magnet.

19. The system of claim 15, wherein the first and second AC driving circuits operate at the same frequency but at either a first and a second distinct predetermined phase offset between the first and second driving coils and where the signal processing apparatus is configured to acquire phase data at the first and second phase offsets.

20. The system of claim 10, wherein the at least one magnetic sensor comprises at least two magnetic sensors positioned to sense field on an axis perpendicular to the driving coils.

21. The system of claim 5, wherein the first AC driving circuit is configured to time multiplex an amplitude of the first driving coil between a first and a second amplitude.

* * * * *